(12) United States Patent
Nyberg et al.

(10) Patent No.: US 10,792,410 B2
(45) Date of Patent: *Oct. 6, 2020

(54) BIOARTIFICIAL LIVER

(71) Applicant: Mayo Foundation for Medical Education and Research, Rochester, MN (US)

(72) Inventors: Scott L. Nyberg, Rochester, MN (US); Stephen M. Corner, Rochester, MN (US); Bruce Amiot, Coon Rapids, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/170,549

(22) Filed: Oct. 25, 2018

(65) Prior Publication Data

US 2019/0184086 A1 Jun. 20, 2019

Related U.S. Application Data

(63) Continuation of application No. 13/256,337, filed as application No. PCT/US2010/027203 on Mar. 12, 2010, now Pat. No. 10,130,748.

(60) Provisional application No. 61/160,150, filed on Mar. 13, 2009.

(51) Int. Cl.
*A61M 1/34* (2006.01)
*C12M 1/00* (2006.01)
*C12M 1/12* (2006.01)

(52) U.S. Cl.
CPC ........ *A61M 1/3472* (2013.01); *A61M 1/3479* (2014.02); *A61M 1/3486* (2014.02); *A61M 1/3489* (2014.02); *C12M 23/02* (2013.01); *C12M 25/16* (2013.01); *A61M 2205/103* (2013.01)

(58) Field of Classification Search
CPC .............. A61M 1/3472; A61M 1/3489; A61M 1/3486; A61M 1/3479; A61M 2205/103; C12M 23/02; C12M 25/16
USPC .......................................................... 422/44
See application file for complete search history.

(56) References Cited

U.S. PATENT DOCUMENTS

| | | | |
|---|---|---|---|
| 3,129,066 | A | 4/1964 | Ambrogi et al. |
| 4,336,329 | A | 6/1982 | Hesse et al. |
| 4,639,422 | A | 1/1987 | Geimer et al. |
| 4,647,539 | A | 3/1987 | Bach |
| 4,804,628 | A | 2/1989 | Cracauer et al. |
| 5,202,254 | A | 4/1993 | Amiot et al. |
| 5,270,192 | A | 12/1993 | Li et al. |
| 5,270,207 | A | 12/1993 | Matsumura et al. |

(Continued)

FOREIGN PATENT DOCUMENTS

| | | |
|---|---|---|
| CN | 201123923 | 1/2008 |
| CN | 101129276 | 2/2008 |

(Continued)

OTHER PUBLICATIONS

Akira and Takeda, "Toll-like receptor signaling," Nat Rev Immunol, 2004, 4:499-511.

(Continued)

*Primary Examiner* — Liban M Hassan
(74) *Attorney, Agent, or Firm* — Fish & Richardson P.C.

(57) ABSTRACT

This document provides bioartificial liver (BAL) devices. Methods for making and using BAL devices also are provided.

10 Claims, 35 Drawing Sheets

Two Hit Hypothesis of Acute Liver Injury

(56) References Cited

U.S. PATENT DOCUMENTS

| | | | |
|---|---|---|---|
| 5,328,614 | A | 7/1994 | Matsumura |
| 5,523,228 | A | 6/1996 | Ingram et al. |
| 5,595,909 | A | 1/1997 | Hu et al. |
| 5,605,835 | A | 2/1997 | Hu et al. |
| 5,624,839 | A | 4/1997 | Yada et al. |
| 5,654,197 | A | 8/1997 | Jem et al. |
| 5,658,797 | A | 8/1997 | Bader |
| 5,981,211 | A | 11/1999 | Hu et al. |
| 6,048,727 | A | 4/2000 | Kopf |
| 6,096,544 | A | 8/2000 | Bramble et al. |
| 6,190,913 | B1 | 2/2001 | Singh |
| 6,218,182 | B1 | 4/2001 | Naughton et al. |
| 6,228,607 | B1 | 5/2001 | Kersten et al. |
| 6,401,552 | B1 | 6/2002 | Elkins |
| 6,544,424 | B1 | 4/2003 | Shevitz |
| 6,544,788 | B2 | 4/2003 | Singh |
| 6,582,955 | B2 | 6/2003 | Martinez et al. |
| 6,602,711 | B1 | 8/2003 | Thomson et al. |
| 7,128,836 | B2 | 10/2006 | De Paolis et al. |
| 7,160,719 | B2 | 1/2007 | Nyberg |
| 8,785,117 | B2 | 7/2014 | Nyberg |
| 2003/0119107 | A1 | 6/2003 | Dang et al. |
| 2003/0228685 | A1 | 12/2003 | Nyberg |
| 2004/0097867 | A1 | 5/2004 | Fraser et al. |
| 2005/0084961 | A1 | 4/2005 | Hedrick et al. |
| 2005/0115898 | A1 | 6/2005 | Sternby et al. |
| 2006/0019385 | A1 | 1/2006 | Smith et al. |
| 2006/0035368 | A1 | 2/2006 | Malinge |
| 2008/0014181 | A1 | 1/2008 | Ariff et al. |
| 2008/0166808 | A1 | 7/2008 | Nyberg |
| 2010/0076380 | A1 | 3/2010 | Hui |
| 2012/0009086 | A1 | 1/2012 | Nyberg |
| 2014/0295548 | A1 | 10/2014 | Nyberg |

FOREIGN PATENT DOCUMENTS

| | | |
|---|---|---|
| CN | 201033178 | 3/2008 |
| EP | 1 063 289 | 12/2000 |
| GB | 2450761 | 1/2009 |
| WO | WO 86/02379 | 4/1986 |
| WO | WO 92/07615 | 5/1992 |
| WO | WO 96/09876 | 4/1996 |
| WO | WO 99/32171 | 7/1999 |
| WO | WO 00/78920 | 12/2000 |
| WO | WO 00/78932 | 12/2000 |
| WO | WO 06/138143 | 12/2006 |

OTHER PUBLICATIONS

Asano et al., "Ultrastructure of Multicellular Spheroids Formed in the Primary Culture of Adult Rat Hepatocytes," J. Clin. Electron Microscopy, 1989, 22(2):243-252.

Brophy et al., "Rat hepatocyte spheroids formed by rocked technique maintain differentiated hepatocyte expression and function," Hepatology, 2009, 49:578-586.

Brunn et al., "Conditional signaling by Toll-like receptor 4," FASEB J, 2005, 19:872-4.

Busse and Gerlach, "Bioreactors for Hybrid Liver Support: Historical Aspects and Novel Designs," Ann. N.Y. Acad. Sci., 1999, 875:326-339.

Carrillo et al., "Multiaggregate Hepatocyte (HP) Spheroids in the Hepato-Cellular Transplant: Structural, Functional and Metabolic Characterization," Transplantation Proceedings, 2001, 33:660-661.

Curcio et al., "Mass transfer and metabolic reactions in hepatocyte spheroids cultured in rotating wall gas-permeable membrane system," Biomaterials, 2007, 28:5487-5497.

De Bartolo et al., "Long-term maintenance of human hepatocytes in oxygen-permeable membrane bioreactor," Biomaterials, 2006, 27:4794-4803.

European Office Action in Application No. 10751502.5, dated Jul. 3, 2017, 7 pages.

European Search Report in Application No. 10751502.5, dated Jun. 13, 2017, 4 pages.

Gerlach et al., "Hepatocyte aggregate culture technique for bioreactors in hybrid liver support systems," Int J Artif Organs., 16(12):843-846, Dec. 1993.

Hong et al., "Effects of Hydrodynamics on Aggregates Formation, Growth and Metabolism of HEK 293 Cells in Suspension Culture," Chin. J Biotech., Jan. 2006, 22(1):101-106.

International Preliminary Report on Patentability in International Application No. PCT/US2010/027203, dated Sep. 22, 2011, 6 pages.

International Search Report and Written Opinion in International Application No. PCT/US2003/17909, dated Feb. 28, 2005, 6 pages.

International Search Report and Written Opinion in International Application No. PCT/US2010/027203, dated Nov. 2, 2010, 9 pages.

Koide et al., "Continued High Albumin Production by Multicellular Spheroids of Adult Rat Hepatocytes Formed in the Presence of Liver-Derived Proteoglycans," Biochem. Biophys. Res. Comm. 1989, 161:385-391.

Koide et al., "Formation of Multicellular Spheroids Composed of Adult Rat Hepatocytes in Dishes with Positively Charged Surfaces and under Other Nonadherent Environments," Exp. Cell Res., 1990, 186:227-235.

Kurosawa, "Methods for Inducing Embryoid Body Formation: In Vitro Differentiation System of Embryonic Stem Cells," J Biosci Bioengineering, 2007, 103(5):389-398.

Lazar et al., "Extended Liver-Specific Functions of Porcine Hepatocyte Spheroids Entrapped in Collagen Gel," In Vivo Cell Dev. Biol., 1995, 31:340-346.

Lazar et al., "Formation of Porcine Hepatocyte Spheroids for Use in a Bioartificial Liver," Cell Transplantation, 1995, 4:259-268.

Leffert and Paul, "Studies on primary cultures of differentiated fetal liver cells," J Cell Biol, 1972, 52:559-568.

Mashberg, T., "A Life-Saving Liver Machine," Technology Review, Mar. 28, 2006, 3 pages, retrieved from http://www.technologyreview.com/read_article.aspx?ch=biotech&sc=&id=16637&pg=1.

Matsumura et al., "Hybrid bioartificial liver in hepatic failure: Preliminary clinical report," Surgery, 1987, 101:99-103.

Mueller-Klieser, "Three-dimensional cell cultures: from molecular mechanisms to clinical applications," Am. J. Physiol., 1997, 273(Cell Physiol. 42):C1109-C1123.

Nishikawa et al., "Comparison of Assay Methods for Benzodiazepines in Urine," Am. J. Clin. Pathol., 1997, 107(3):345-352.

Notice of Allowance in U.S. Appl. No. 10/164,817, dated Sep. 6, 2006, 4 pages.

Notice of Allowance in U.S. Appl. No. 11/562,008 dated Sep. 6, 2013, 8 pages.

Nyberg et al., "Brain lactate by magnetic resonance spectroscopy during fulminant hepatic failure in the dog," Liver TransplantatNion and Surgery, 1997, 4:158-165.

Nyberg et al., "Rapid, Large-Scale Formation of Porcine Hepatocyte Spheroids in a Novel Spheroid Reservoir Bioartificial Liver," Liver Transplantation, 2005, 11(8):901-910.

Office Action and Search Report in Chinese Application No. 201080019388X dated Nov 15, 2013, 20 pages.

Office Action in U.S. Appl. No. 10/164,817, dated Aug. 9, 2006.
Office Action in U.S. Appl. No. 10/164,817, dated Dec. 15, 2004.
Office Action in U.S. Appl. No. 10/164,817, dated Feb. 22, 2006.
Office Action in U.S. Appl. No. 10/164,817, dated Jun. 15, 2005.
Office Action in U.S. Appl. No. 11/562,008, dated May 21, 2009.
Office Action in U.S. Appl. No. 11/562,008, dated Nov. 3, 2009.
Office Action in U.S. Appl. No. 13/256,337, dated Dec. 21, 2015, 20 pages.
Office Action in U.S. Appl. No. 13/256,337, dated Feb. 1, 2013, 18 pages.
Office Action in U.S. Appl. No. 13/256,337, dated Jun. 17, 2014, 23 pages.
Office Action in U.S. Appl. No. 13/256,337, dated Sep. 6, 2013, 23 pages.
Office Action in U.S. Appl. No. 14/307,039, dated Oct. 23, 2015, 10 pages.

Ota et al., "Xenotransplantation of Spheroidal Aggregate-Cultured Hepatocytes," Trans. Proc., 1997, 29:912-913.

(56) References Cited

OTHER PUBLICATIONS

Ramm, "Isolation and culture of rat hepatic stellate cells," J Gastroenterol Hepatol, 1998, 13:846-851.

Rifkind, "Studies on the interaction between endotoxin and polymyxin B," J Infectious Dis, 1967, 117:433-438.

Saito et al., "Transplantation of Spheroidal Aggregate Cultured Hepatocytes into the Rat Spleen," Trans. Proc., 1989, 21:2374-2377.

Sakaguchi et al., "Promotion of Spheroid Asembly of Adult Rat Hepatocytes by Some Factor(s) Present in the Initial 6-Hour Conditioned Medium of the Primary Culture," Pathobiology, 1991, 59:351-356.

Sakai et al., "A New Bioartificial Liver Using Porcine Hepatocyte Spheroids in High-Cell-Density Suspension Perfusion Culture: In Vitro Performance in Synthesized Culture Medium and in 100% Human Plasma," Cell Trans., 1999, 8:531-541.

Sauer et al., "Clinical extracorporeal hybrid liver support—phase I study with primary porcine liver cells," Xenotransplantation, 2003, 10:460-469.

Seglen, "Preparation of isolated rat liver cells," Methods Cell Biol., 1976, 13:29-83.

Shinji et al. "Glycosaminoglycans Partially Substitute for Proteoglycans in Spheroid Formation of Adult Rat Hepatocytes in Primary Culture," Cell Structure and Function, 1988, 13:179-188.

Sielaff et al., "A Technique for Porcine Hepatocyte Harvest and Description of Differentiated Metabolic Functions in Static Culture," Transplantation, 1995, 59(10):1459-1463.

Sielaff et al., "Application of a bioartificial liver (BAL) in a new model of acute fulminant hepatitis," Surgical Forum, 1993, 44:61-63.

Spiegelberg and Bishop, "Tissue-specific gene expression in mouse hepatocytes cultured in growth-restricting medium," Mol Cell Biol, 1988, 8:3338-3344.

Stadlbauer et al., "Artificial Liver Support Systems in the Management of Complications of Cirrhosis," Seminars in Liver Disease, 2008, 28(1):96-109.

Strain and Neuberger, "A Bioartificial Liver—State of the Art," Science, 2002, 295:1005-1009.

Termeer et al., "Oligosaccharides of hyaluronan are potent activators of dendritic cells," J Immunol, 2000, 165:1863-1870.

Valatas et al., "Isolation of rat Kupffer cells: a combined methodology for highly purified primary cultures," Cell Biol International, 2003, 27:67-73.

Wheaton Glass Roller Culture Vessels. Datasheet [online]. Fisher Scientific Inc., 2014 [retrieved on Oct. 19, 2015]. Retrieved from the Internet: <URL: https://www.fishersci.com/shop/products/wheaton-glass-roller-culture-vessels-5/p-177149>.

Wu et al., "Entrapment of Hepatocyte Spheroids in a Hollow Fiber Bioreactor as a Potential Bioartificial Liver," Tissue Engineering, 1995, 1:29-40.

Yagi et al., "Caspase Inhibition Reduces Apoptotic Death of Cryopreserved Porcine Hepatocytes," Hepatology, 2001, 33:1432-1440.

Yin et al., "Derivation, Characterization, and Phenotypic Variation of Hepatic Progenitor Cell Lines Isolated From Adult Rats," Hepatology, 2002, 35:315-324.

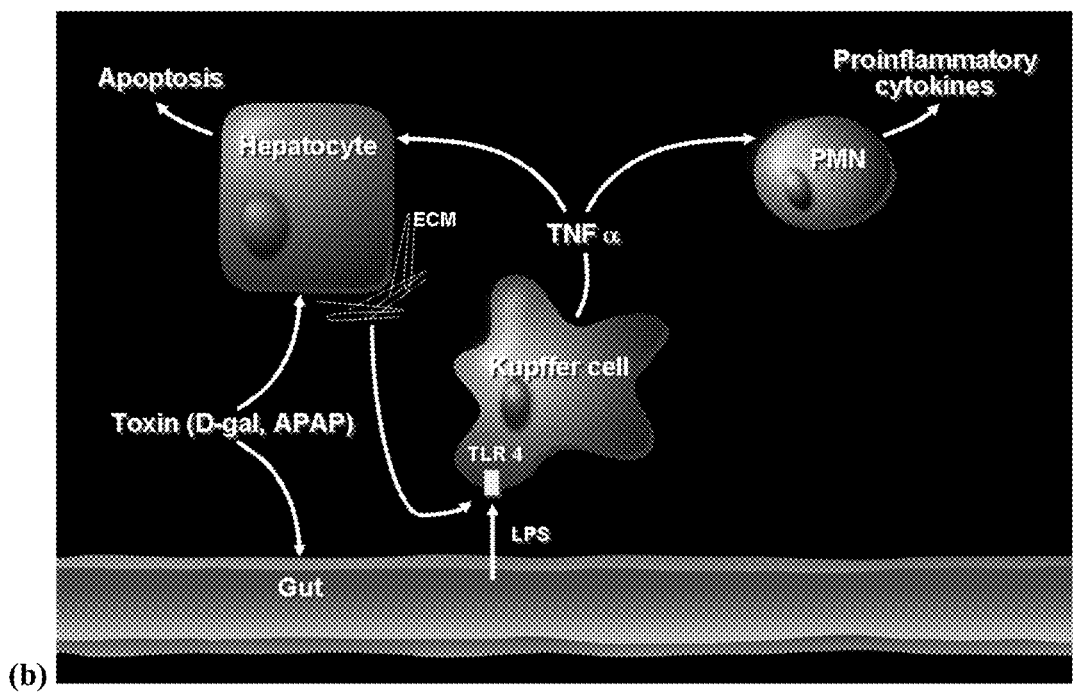
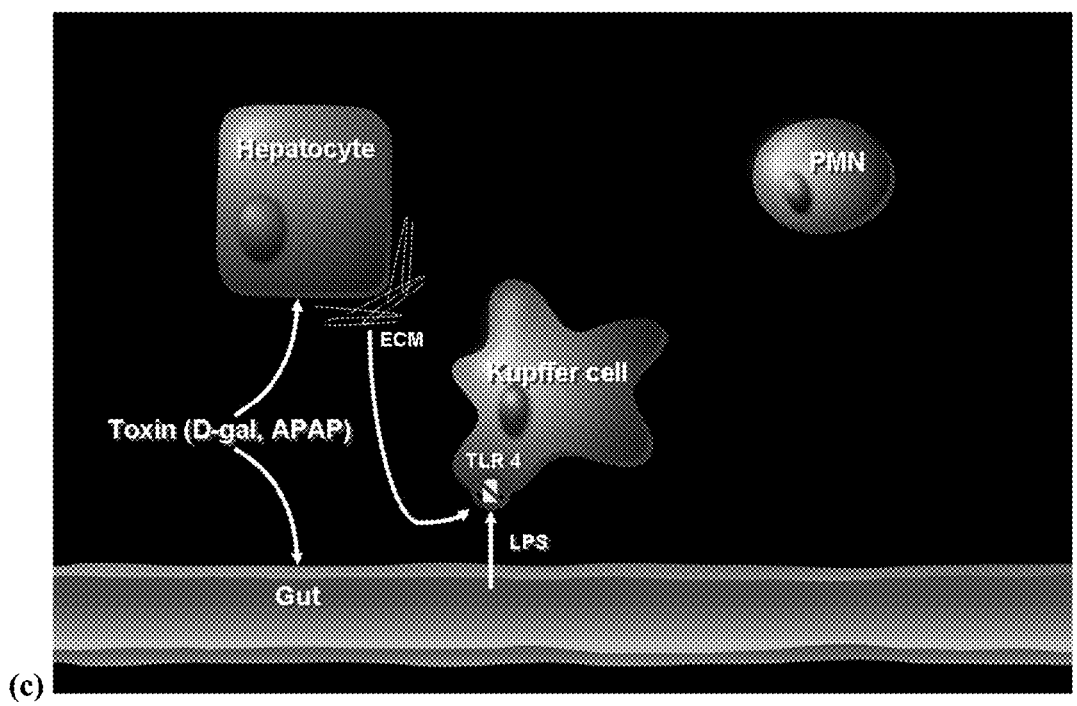
Figs. 6(b)&(c)

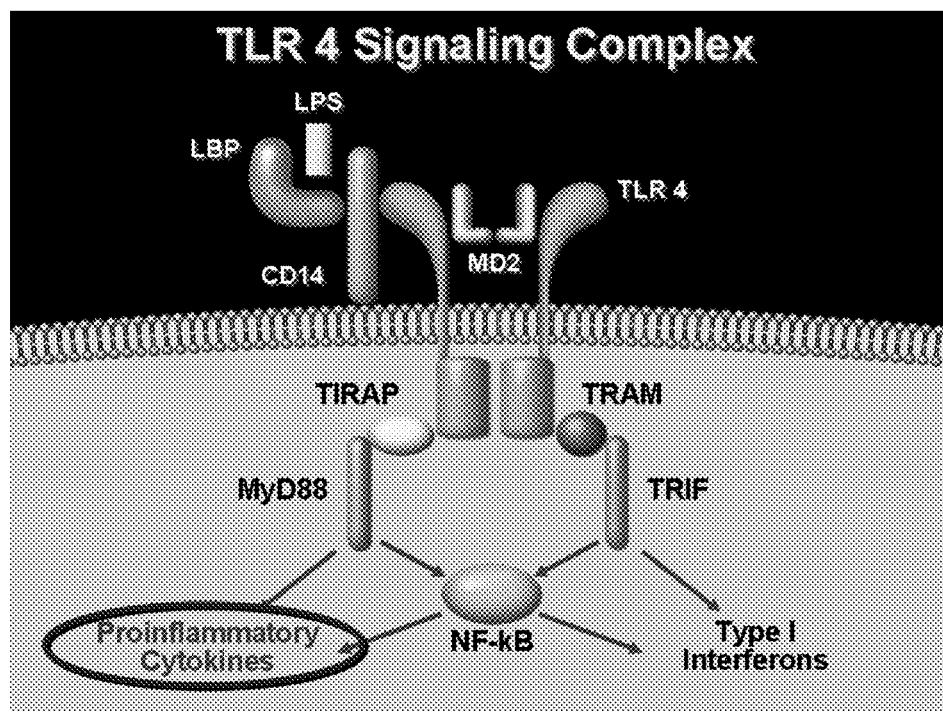
(a)
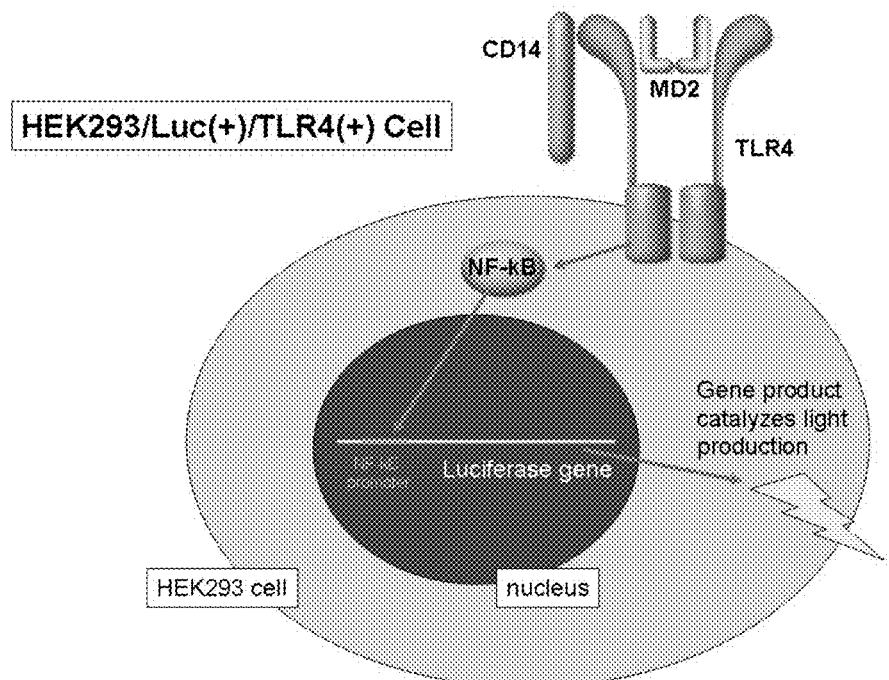
(b)
Figs. 7(a)&(b)

(a)

(b)

(c)

| O$_2$ Consumption | ΔmmHg | μmol O$_2$/min | % of baseline |
|---|---|---|---|
| Day 0 | | 142.3 | 100% |
| Day 1 | | 101.3 | 71% |
| Day 2 | | 92.6 | 65% |
| SRBA | 0 | 63 | |
| L t=4hr | 400 | 26 | 42.3 | 100% |
| t=0h#5hr | 400 | 22 | 21.6 | 51% |
| t=16hr | 400 | 19 | 18.3 | 43% |
| t=22hr | 400 | 28 | 15.8 | 37% |
| t=24hr | 400 | 20 | 23.3 | 55% |
| | | | 16.6 | 39% |

Fig. 18

|  | Hepatocyte Total Volume Day 0 | Culture Total Volume Day 1 | Culture Total Volume Day 2 |
| --- | --- | --- | --- |
| Tray 1 | 15.4 | 11.0 | 11 |
| Tray 2 | 15.6 | 15.1 | 10.2 |
| Tray 3 | 14.5 | 11.7 | 10 |
| Tray 4 | 15.0 | 18.3 | 12.9 |
| mean | 15.1 | 14.0 | 11.0 |
| st dev | 0.5 | 3.3 | 1.3 |
| p value |  | 0.5322 | 0.1477 | volumes= ## x $10^9$ $\mu m^3$

Fig. 19

|  | % spheroids Day 1 | % spheroids Day 2 |
|---|---|---|
| Tray 1 | 95.1% | 95.5% |
| Tray 2 | 93.9% | 92.4% |
| Tray 3 | 90.3% | 91.1% |
| Tray 4 | 95.6% | 93.8% |
| mean | 93.7% | 93.2% |
| st dev | 2.4% | 1.9% |

Fig. 20

BIOARTIFICIAL LIVER

CROSS-REFERENCE TO RELATED APPLICATIONS

This application is a continuation of U.S. application Ser. No. 13/256,337 (now U.S. Pat. No. 10,130,748), filed Sep. 13, 2011, which is a National Stage application under 35 U.S.C. § 371 of International Application No. PCT/US2010/027203, filed Mar. 12, 2010, which claims the benefit of U.S. Provisional Application Ser. No. 61/160,150, filed on Mar. 13, 2009. The disclosures of the prior applications are considered part of (and are incorporated by reference in) the disclosure of this application.

STATEMENT AS TO FEDERALLY SPONSORED RESEARCH

This invention was made with government support under DK 056733 awarded by the National Institutes of Health. The government has certain rights in the invention.

TECHNICAL FIELD

This document relates to bioartificial livers.

BACKGROUND

According to the annual report of the American Liver Foundation in 2000, hepatitis and other liver diseases affect 25 million Americans. Liver failure is the 8th most frequent cause of death in the United States, accounting for roughly 43,000 deaths each year. Liver transplantation is currently the only effective treatment for medically refractory liver failure. Liver transplantation has some shortfalls, however, including a shortage of donor organs, restrictions on potential recipients, and side effects of drugs used to prevent rejection after transplantation. The problem of organ scarcity is demonstrated by the fact that nearly 2000 candidates for liver transplantation died on the waiting list in 2003. Over 500 of these patients were listed with a diagnosis of fulminant hepatic failure (FHF). One potential solution to the shortage of organs is an extracorporeal liver support system, or bioartificial liver (BAL), which could serve as a bridge to transplantation or, in some cases, until spontaneous recovery of the native liver.

One goal of BAL therapy is to provide detoxification activity and preventing the systemic manifestations of acute liver injury as illustrated in FIG. 1. Current knowledge is that extrahepatic manifestations of ALF, such as brain edema, lung dysfunction, and renal dysfunction, result from a two-hit process: 1) systemic inflammatory response syndrome (SIRS); 2) occurring in the setting of inadequate hepatic synthetic and detoxification activities. The inflammatory response of ALF is mediated by cytokines, such as TNFα, that can be released from the acutely injured liver, while toxins such as ammonia apply a direct cytotoxic influence on target organs and their supporting cells. In support of this theory is the observation that SIRS is seen in at least 60% of ALF cases.

Ammonia, normally eliminated by the liver, is the most important toxin of the two-hit hypothesis outlined in FIG. 1. Arterial concentrations of ammonia have been shown to correlate with cerebral herniation in pediatric patients with urea cycle disorders and in many, but not all, ALF patients. TNFα is also an important marker of SIRS and the two-hit hypothesis of ALF. Furthermore, cytokines such as TNFα are believed to mediate the local inflammatory response and brain edema of head trauma. Therefore, it is highly conceivable that a synergism exists between inflammation and ammonia resulting in extrahepatic manifestations of ALF, such as brain edema.

SUMMARY

This document provides spheroid reservoir bioartificial livers (SRBALs), methods of making SRBALs, and methods for using SRBALs. In some cases, the SRBALs described herein can include a multi-shelf rocking device that is configured to rock a plurality of cell containers for forming hepatocyte spheroids. In some cases, the SRBALs described herein can include a reservoir chamber for housing hepatocyte spheroids that has a screen member to allow bi-directional fluid flow. In some cases, the a screen member can be designed to prevent loss of hepatocyte spheroids from the reservoir chamber. The screen member can be a membrane, a filter, or a mesh with openings in the micron range. In some cases, the reservoir chamber can include a fenestrated funnel-shaped settling column or cylindrical shaped settling column to prevent loss of spheroid hepatocytes into the outflow leaving the reservoir. In some cases, the SRBALs described herein can be liver support devices that combine liver cell therapy with albumin dialysis to create a hybrid system that addresses past limitations of both forms of extracorporeal artificial liver therapy. In such SRBALs, albumin dialysis and primary hepatocytes can be synergistic for treatment of ALF.

In general, one aspect of this document features a bioartificial liver device comprising a reservoir chamber configured to house hepatocyte spheroids, wherein the reservoir chamber comprises a mixing chamber and a settling volume chamber, wherein the mixing chamber is separated from the settling volume chamber by a funnel, and wherein the mixing chamber is in fluid communication with the settling volume chamber via at least one opening defined in the funnel. The funnel can be a fenestrated funnel. The fenestrated funnel can comprise openings between 100 µm and 5 mm in diameter. The reservoir chamber can comprise a magnetic stir bar within the mixing chamber. The mixing chamber can comprise an inlet port. The settling volume chamber can comprise an outlet port. The funnel can comprise more than 25 openings. The openings can be between 100 µm and 5 mm in diameter. The reservoir chamber can comprise a sampling port. The reservoir chamber can comprise temperature probe.

In another aspect, this document features a bioartificial liver device that includes a plurality of cell containers to form hepatocyte spheroids. The device can also include a multi-shelf rocking device that is configured to rock the plurality of cell containers. The device can further include a reservoir chamber that is configured to house the hepatocyte spheroids after they are formed in the plurality of cell containers.

In some embodiments, the bioartificial liver device can also include an albumin dialysis system. In some embodiments, the albumin dialysis system can include a blood separation cartridge, a charcoal column, a resin column, and a dialysis membrane. In some embodiments, the albumin dialysis system can include a pre-dilution circuit.

In some embodiments, the multi-shelf rocking device can be configured to rock at about 5-20 cycles/min. In some embodiments, the multi-shelf rocking device can include one or more rocker boxes having a membrane for gas inflow/outflow.

In some embodiments, the reservoir chamber can include a mixing device (e.g., a spinning device or an impeller/propeller device) to maintain hepatocyte spheroids in suspension. In some embodiments, the reservoir chamber can be configured to allow bi-directional fluid flow.

In another aspect, this document features a bioartificial liver device that includes a reservoir chamber that is configured to house hepatocyte spheroids and includes a membrane to allow bi-directional fluid flow. In some embodiments, the membrane can have a pore size in the micron range (e.g., about 20-40 microns or smaller).

In some embodiments, the bioartificial liver device can also include an albumin dialysis system. In some embodiments, the albumin dialysis system can include a blood separation cartridge, a charcoal column, a resin column, and a dialysis membrane. In some embodiments, the albumin dialysis system can include a pre-dilution circuit.

In some embodiments, the bioartificial liver device can also include a multi-shelf rocking device that is configured to rock a plurality of cell containers to form hepatocyte spheroids. In some embodiments, the reservoir chamber can also include a mixing device configured to maintain hepatocyte spheroids in suspension. In some embodiments, the reservoir chamber can also include a gas permeable membrane to facilitate gas exchange.

In another aspect, this document features a bioartificial liver device that includes an albumin dialysis system. The device can also include a reservoir chamber that is in fluid communication with the albumin dialysis system and is configured to house hepatocyte spheroids.

In some embodiments, the albumin dialysis system can include a blood separation cartridge, a charcoal column, a resin column, and a dialysis membrane. In some embodiments, the albumin dialysis system can include a pre-dilution circuit.

In some embodiments, the bioartificial liver device can also include a multi-shelf rocking device that is configured to rock a plurality of cell containers to form hepatocyte spheroids.

In some embodiments, the reservoir chamber can include a mixing device to maintain hepatocyte spheroids in suspension. In some embodiments, the reservoir chamber can include a screen (e.g., a membrane, a filter, or a mesh with openings in the micron range) that is configured to allow bi-directional fluid flow or that is configured to prevent loss of spheroid hepatocytes from the reservoir chamber. In some cases, the reservoir chamber can be designed to function as a settling column to prevent loss of hepatocyte spheroids. In some embodiments, the reservoir chamber can include a gas permeable membrane to facilitate gas exchange. In some cases, a screen or spacer can be located between the gas permeable membrane and the inner wall of the reservoir to allow uniform gas flow through the device.

In some embodiment, the bioartificial liver device can also include a controller to stabilize fluid volume in the reservoir chamber.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6(a)-6(c): Role of TLR4 in signaling liver injury and SIRS after toxin exposure.

FIGS. 7(a)-7(c): (a) TLR4 Signaling Complex is found in many cell types. It can also be stably transfected into reporter cells to measure TLR4 agonist activity in vitro; (b) is a schematic representation of HEK293 cells which have been transfected with TLR4 complex and a luciferase reporter gene to measure TLR4 agonist activity in vitro. The HEK293/Luc(+)/TLR4(+) cells, used to measure TLR4 agonist activity in mouse serum in (c) are used to screen dog serum for TLR4 agonist activity; (c) TLR4 agonist activity was elevated in mouse blood after toxic exposure to APAP (500 vs 0 mg/kg). This in vitro assay is based on a luciferase reporter gene linked to NFκβ in HEK293 cells which responds to TLR4 activation. Only trace background activity was detected in HEK293 cells lacking the TLR4 complex, labeled TLR4(−), confirming specificity of the luciferase activity to TLR4.

FIG. 18: Table providing oxygen consumption results of pig hepatocyte spheroids in culture in the multishelf rocker (Day 0, 1, 2) and the fenestrated funnel settling column reservoir (hours 0-24).

FIG. 19: Table providing data demonstrating stable cell volume during spheroid formation under low $pO_2$ conditions.

FIG. 20: Table providing data demonstrating high yield of spheroids from pig hepatocytes under low $pO_2$ conditions.

DETAILED DESCRIPTION

Figure 1:
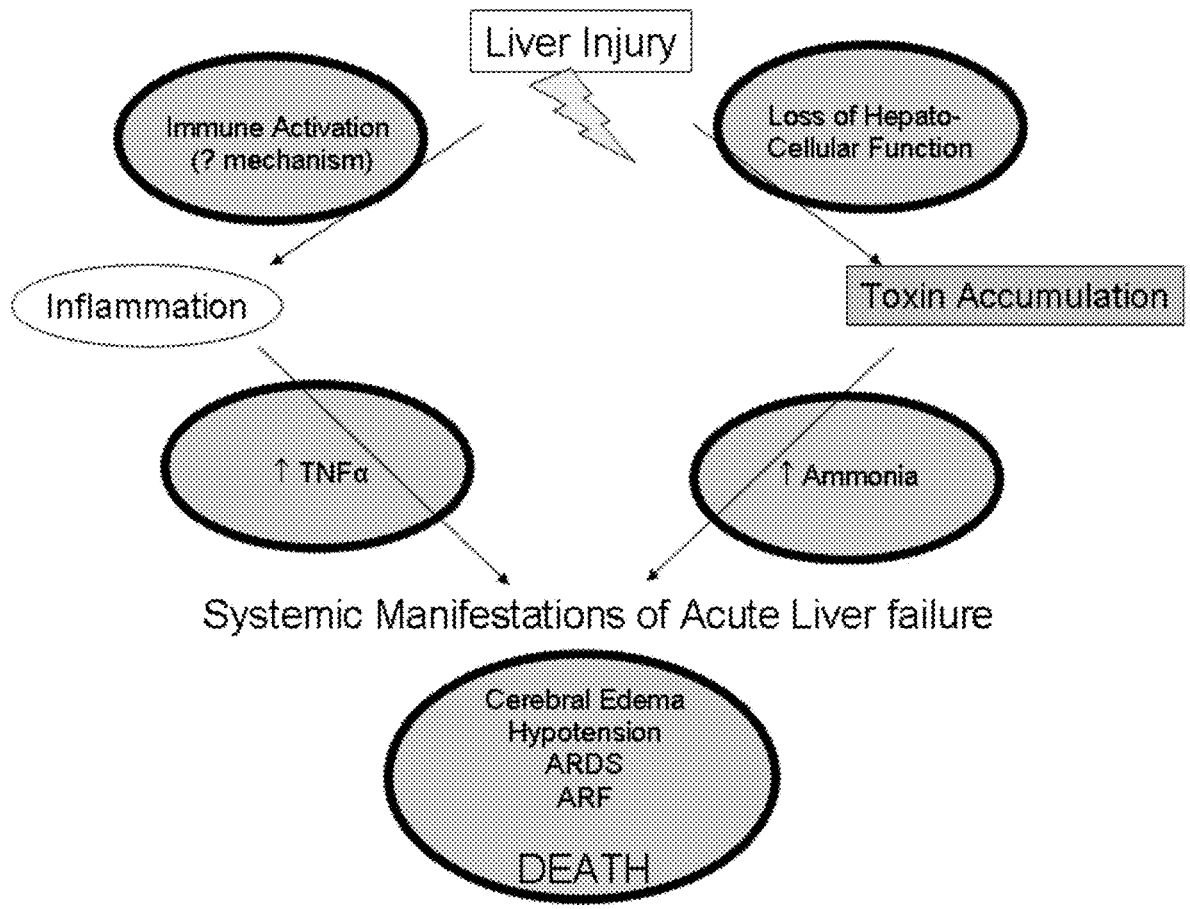
FIG. 1: The two-hit hypothesis suggests that the systemic manifestations of acute liver injury which may include cerebral edema, fever, hypotension, lung dysfunction, renal failure, and death result from a synergistic accumulation of toxins after loss of hepatocellular function (i.e., ammonia accumulation from loss of ureagenesis) and a systemic inflammatory response of unclear etiology but not likely to be infectious in origin. Data indicates that the SRBAL prevents the systemic manifestations of acute liver injury by correcting both arms of this process.
Figure 2:
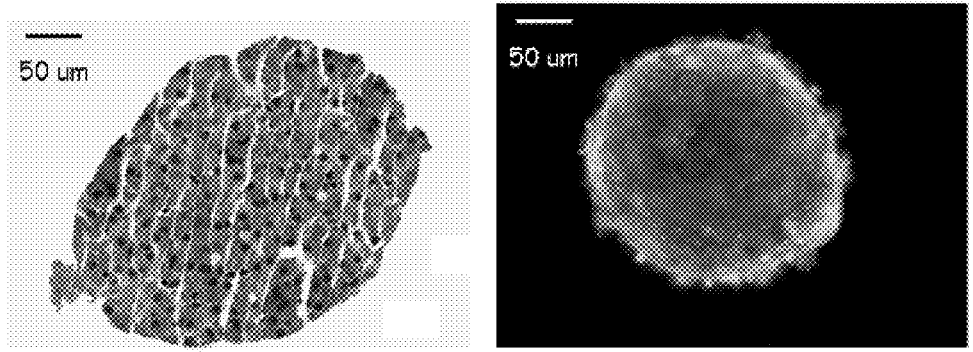
FIG. 2: Pig hepatocyte spheroids provide the metabolic and detoxification activity to the SRBAL device. Examples of porcine hepatocyte spheroids are shown after 1 week in the rocked cultured system which is utilized in an exemplary SRBAL device.
Figure 3A:
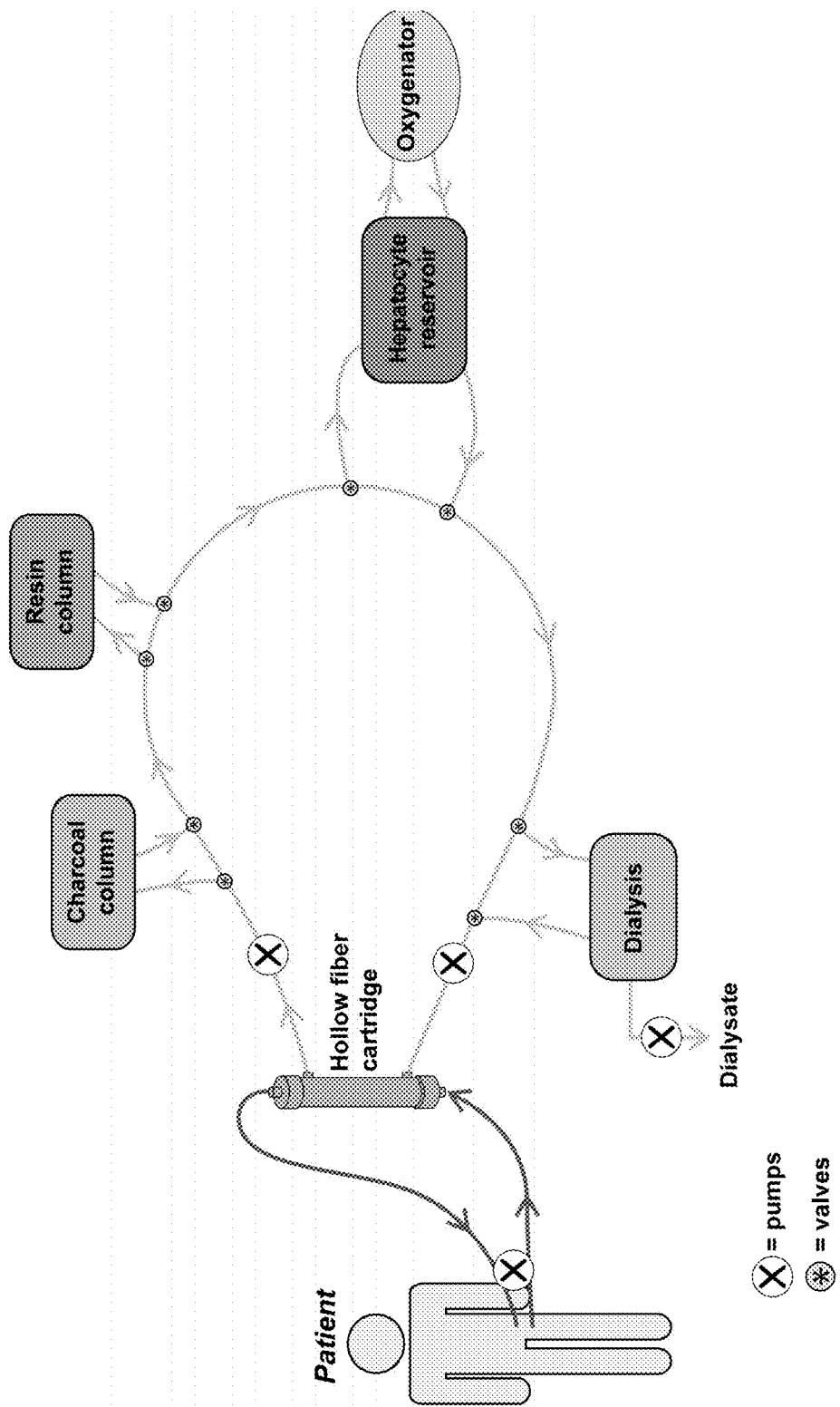
FIGS. 3(a)-3(c): Schematic (a), photographic (b), and diagrammatic (c) illustrations of an exemplary SRBAL device for use in, for example, preclinical trials. The SRBAL is a "hybrid" extracorporeal liver support device that includes an albumin dialysis system and a living biological component. The hepatocyte reservoir can have spheroids of primary porcine hepatocytes. The 5-pump SRBAL device places the hepatocyte reservoir into the albumin perfusate of a standard albumin dialysis extracorporeal configuration. The albumin perfusate circuit includes charcoal and resin columns as currently configured in the MARS™ circuit (Gambro, Lund Sweden).
Figure 3B:
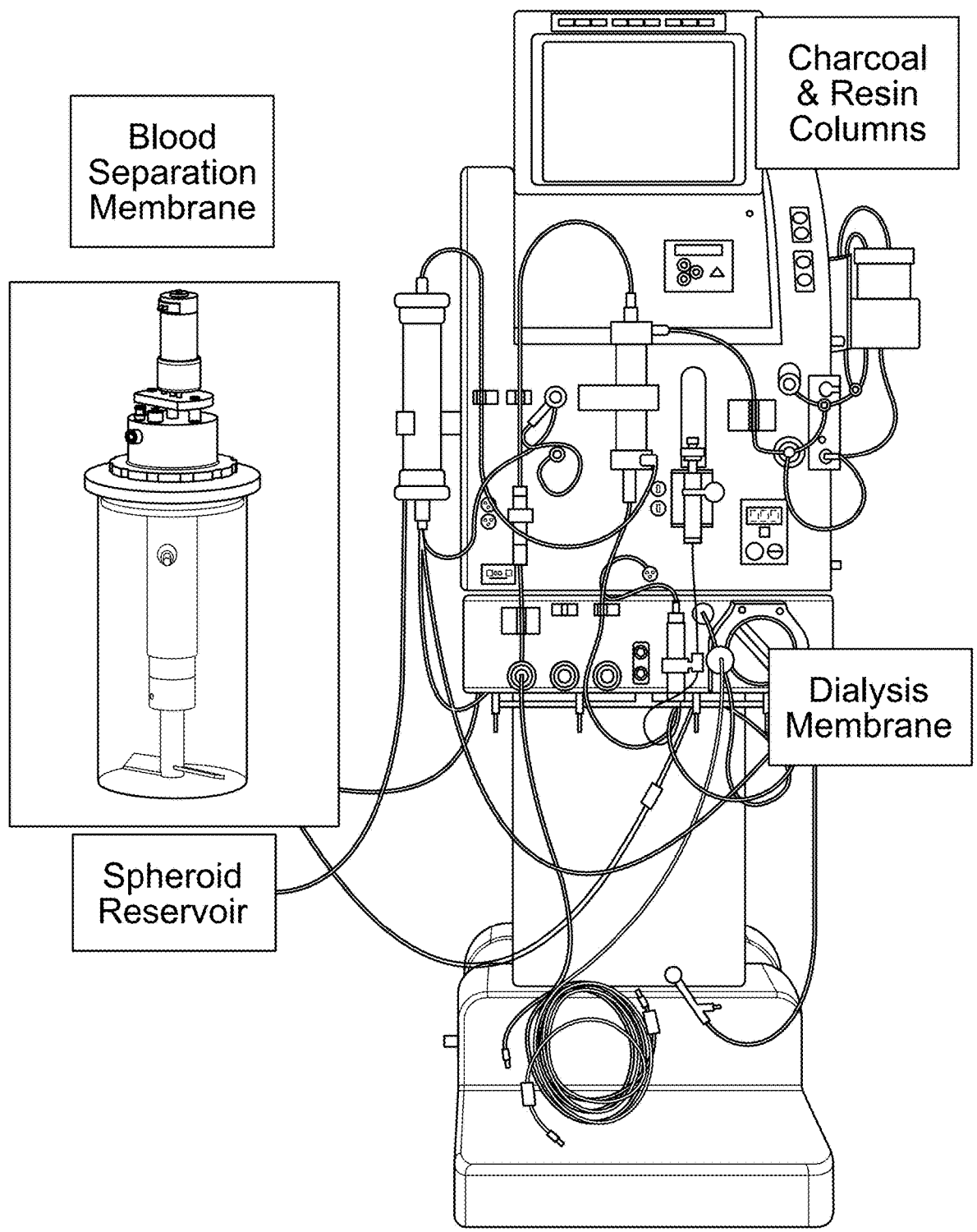

A SRBAL provided herein is an extracorporeal artificial liver device. In some cases, a SRBAL provided herein can include a multi-shelf rocking device for forming hepatocytes spheroids. In some cases, a SRBAL provided herein can include a screen or mesh with micron sized openings that allows bi-directional fluid flow. In some cases, the spheroid reservoir chamber can include a fenestrated funnel settling column to prevent loss of hepatocyte spheroids from the chamber. In some cases, a SRBAL provided herein can include an albumin dialysis system. The albumin dialysis system of the device can be analogous to the MARS® albumin dialysis system produced by Gambro, Inc (Lund, Sweden) with the modification of a larger pore size membrane (150 kD-400 kD) or smaller and addition of a Dialysis Hollow Fiber Filter for ultrafiltration, pre-dilution, and convective mass transfer across the Blood hollow fiber membrane filter. In some cases, a SRBAL provided herein can include a living biological component (e.g., hepatocytes obtained from mammalian livers including human, equine, canine, porcine, bovine, ovine, and murine sources). For example, the living biological component can have porcine hepatocytes in a 3-dimensional tissue construct (i.e., spheroid) as illustrated in FIG. 2. The spheroid aggregate design can be as described in U.S. Pat. No. 7,160,719 to Nyberg. The spheroids of porcine hepatocytes can be isolated in a reservoir chamber located in continuity with an albumin perfusate of the albumin dialysis system. An example of a SRBAL device is illustrated schematically, photographically, and diagrammatically in FIGS. 3a, 3b, and 3c, respectively. Another example of a SRBAL device provided herein is illustrated diagrammatically and photographically in FIGS. 14a and 14b, respectively.

Figure 3C:
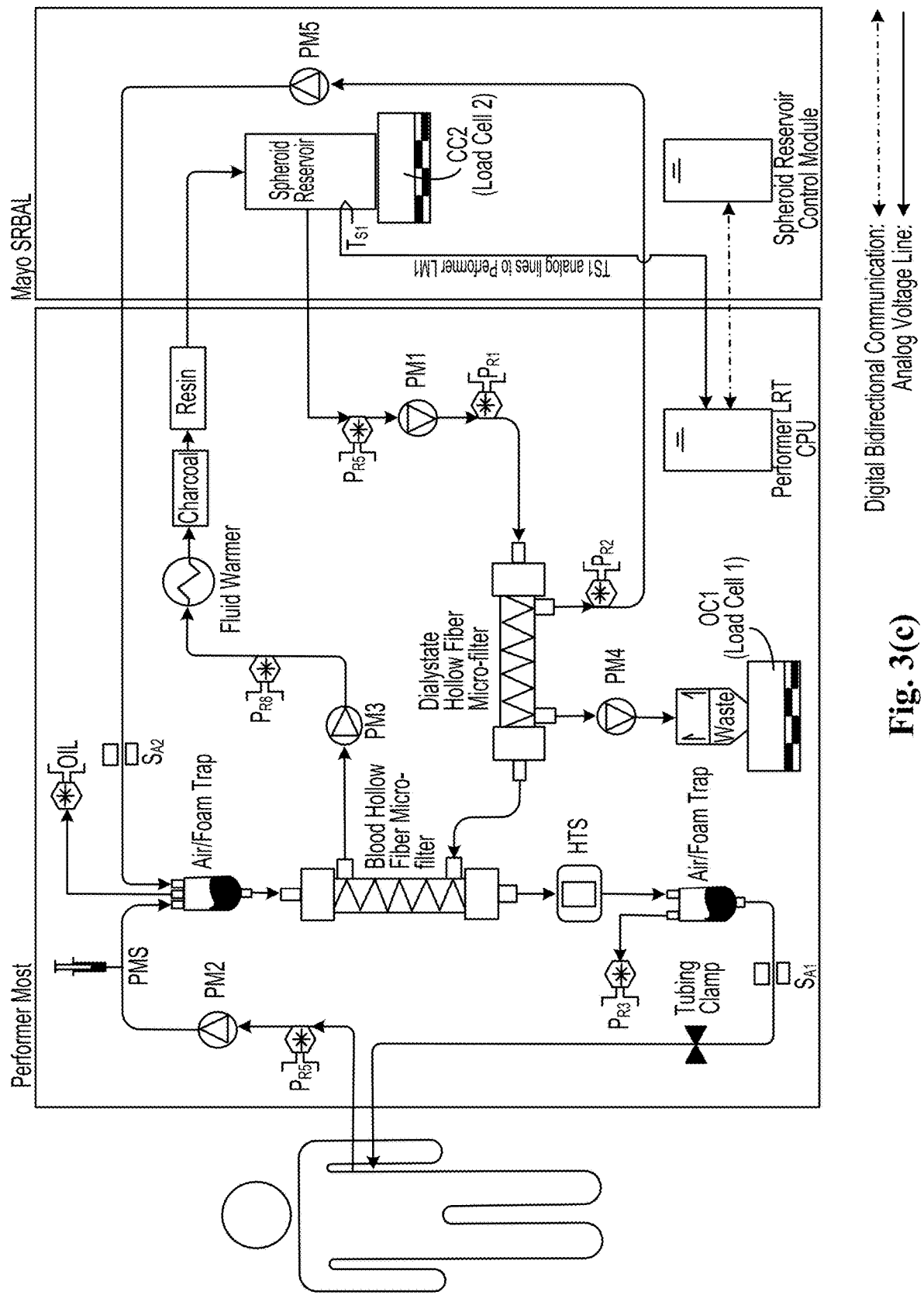

The SRBAL device can be designed for continuous extracorporeal therapy of patients with liver failure. The patient's blood circulation may be connected to the device by a two-lumen venovenous catheter which is able to achieve blood perfusion rates on the order of 100-200 mL/min. The device can operate analogous to continuous venovenous hemodialysis. In this exemplary embodiment, the device contains five pumps as illustrated in FIG. 3(c) (pumps labeled PM1-5). Pumps 1 and 3 are used to perfuse the albumin circuit. Pump 2 perfuses blood from the patient to the hollow fiber blood separation cartridge. Pump 4 is used for discard of ultrafiltration fluid as needed to maintain the patient's fluid status—analogous to continuous venovenous hemodialysis. Pump 5 controls a pre-dilution circuit used to achieve high ultrafiltration rates across the hollow fiber membrane which is located at the intersection of the patient blood circuit and the albumin circuit.

Figure 14A:
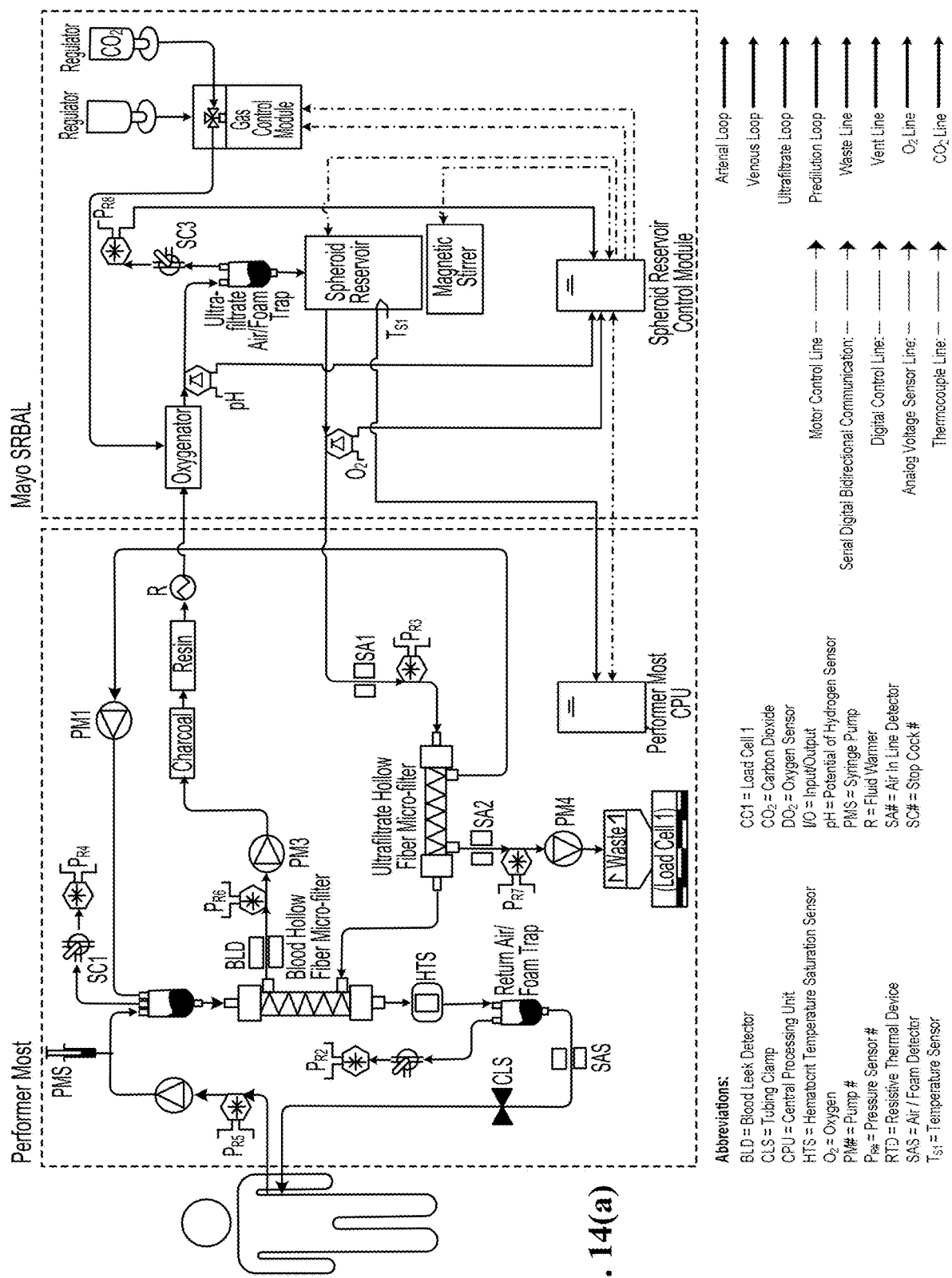
FIGS. 14(a)-14(b): Diagrammatic (a) and photographic (b) illustration of an exemplary SRBAL device having four pumps. The SRBAL is a "hybrid" extracorporeal liver support device that includes an albumin dialysis system and a living biological component. The hepatocyte reservoir can have hepatocyte spheroids.
Figure 14B:
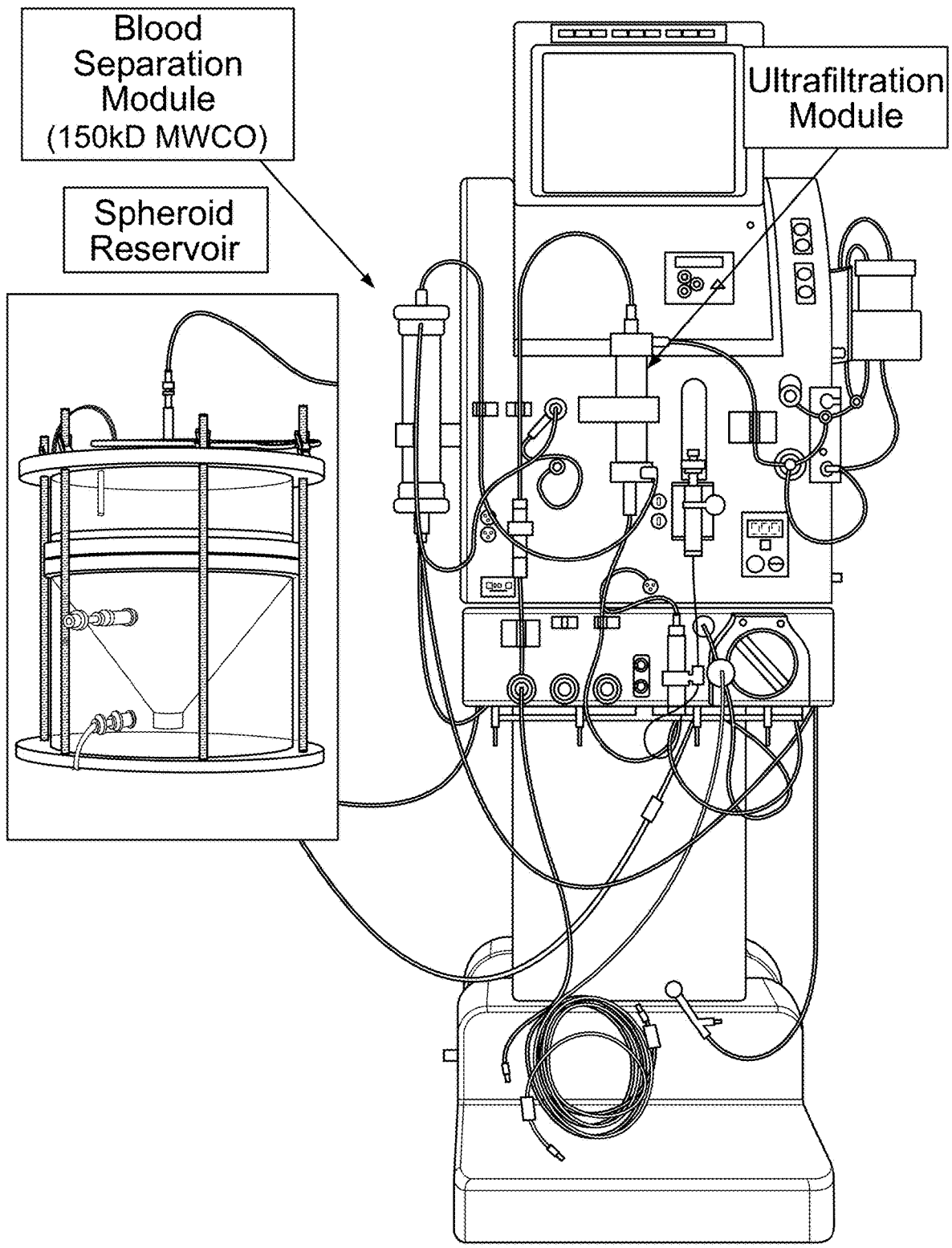

In some cases, the device can be designed to have four pumps as illustrated in FIG. 14a (pumps labeled PM1-4). Pump 3 is used to perfuse the albumin circuit. Pump 2 perfuses blood from the patient to the hollow fiber blood separation cartridge. Pump 4 is used for discard of ultrafiltration fluid as needed to maintain the patient's fluid status—analogous to continuous venovenous hemodialysis. Pump 1 controls a pre-dilution circuit used to achieve high ultrafiltration rates across the hollow fiber membrane which is located at the intersection of the patient blood circuit and the albumin circuit. In some cases, the device can include an air/foam trap positioned above the spheroid reservoir as shown in FIG. 14a.

Along with the spheroid reservoir, the albumin circuit includes a charcoal column, a resin column, a fluid warmer, and a second hollow fiber membrane module for ultrafiltration. The device can be microprocessor controlled to stabilize fluid volumes in the spheroid reservoir and accomplish ultrafiltration if desired for fluid removal. The device can include various controllers to regulate temperature, pH and/or $O_2$. The SRBAL device can provide multiple aspects of extracorporeal liver support including detoxification of waste materials from the patient and delivery of water metabolites and growth factors and other, as yet unidentified products of primary liver cells back to the patient. These processes may involve mass transport across the hollow fiber membrane by both diffusion and convection. Diffusion can be primarily determined by the surface area of the hollow fiber membrane and the concentration gradient across the membrane, while convection can be determined by the flow of fluid across the membrane set by pumping conditions.

In some implementations, a dose of 200-400 g hepatocytes (e.g., porcine hepatocytes) is used in the SRBAL. The dose can be prepared by starting with $5-10 \times 10^6$ cells/mL in 6-12 liters of medium placed in a multi-shelf rocker device, then concentrating to put $1-2 \times 10^7$ cells/mL (e.g. approximately 200-400 g) in a 3 L spheroid reservoir. In some implementations, the albumin concentration may be in a range of 0.5 to 5.0 g/dL. In some implementations, the albumin circuit can include a pre-dilution feature such as a circuit off of the Dialysis Hollow Fiber Membrane Filter to the inlet air/foam trap and involving pump 5 shown in FIG. 3c. Pre-dilution may allow for convective flow across the membrane of the Blood Hollow Fiber Membrane filter without excessive hemoconcentration and sludging of blood in the patient's blood circuit. Increased mass transfer from the patient to the albumin circuit and hepatocyte reservoir can have the benefit of increased detoxification by the SRBAL. In some implementations, pumps 1 and 3 (PM1 and PM3) as shown in FIG. 3c are operated at the same rate—a rate that circulates fluid to and from the hepatocyte spheroid reservoir increase difussive mass transfer. In some implementations, pump 4 (PM4) as shown in FIG. 3c may be set to remove fluid based on a clinical need (e.g., renal replacement outflow). In some implementations, pump 5 (PM5; recycle circuit) as shown in FIG. 3c may be set to provide predilution and better mass transfer across the hollow fiber membrane via convective flow. The flow rate of pump 5 as shown in FIG. 3c can determine how much ultrafiltrate fluid from the albumin circuit is recycled to the inlet of the Blood Hollow Fiber membrane filter for predilution while pump 4 as shown in FIG. 3c determines how much fluid is removed from the patient. The spheroid reservoir volume can be held constant during standard operating conditions. Together, the rates of pump 4 and pump 5 can determine the rate of convective flow (F) across the hollow fiber membrane. If pump 4 and pump 5 are set at 0 mL/min, then there is no convection flow across the hollow fiber membrane (F=0), and mass transport occurs by pure diffusion. If pump 4 and/or pump 5 are in operation, then convection occurs across the hollow fiber membrane. Under standard conditions, the blood separation hollow fiber filter can have pores of 150 kD-400 kD. This pore size is larger than MARS™ (70 kD; Gambro, Lund Sweden).

In some cases, the device can have four pumps as shown in FIG. 14.

Figure 4A:
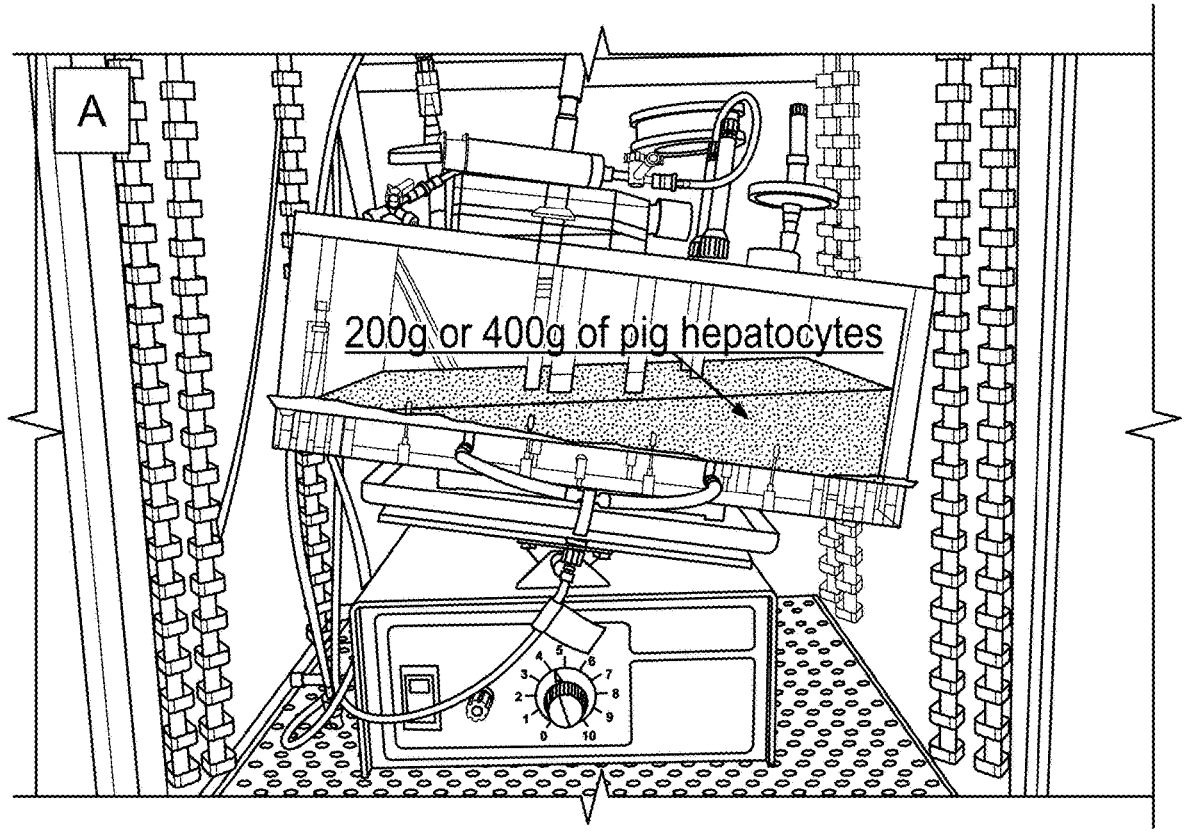
FIGS. 4(a)-4(d): Spheroid reservoir configurations: (a) rocker reservoir for spheroid formation; (b) multi-shelf rocker for large-scale spheroid formation; (c) spinner reservoir for extracorporeal use; and (d) schematic of spinner reservoir.
Figure 4B:
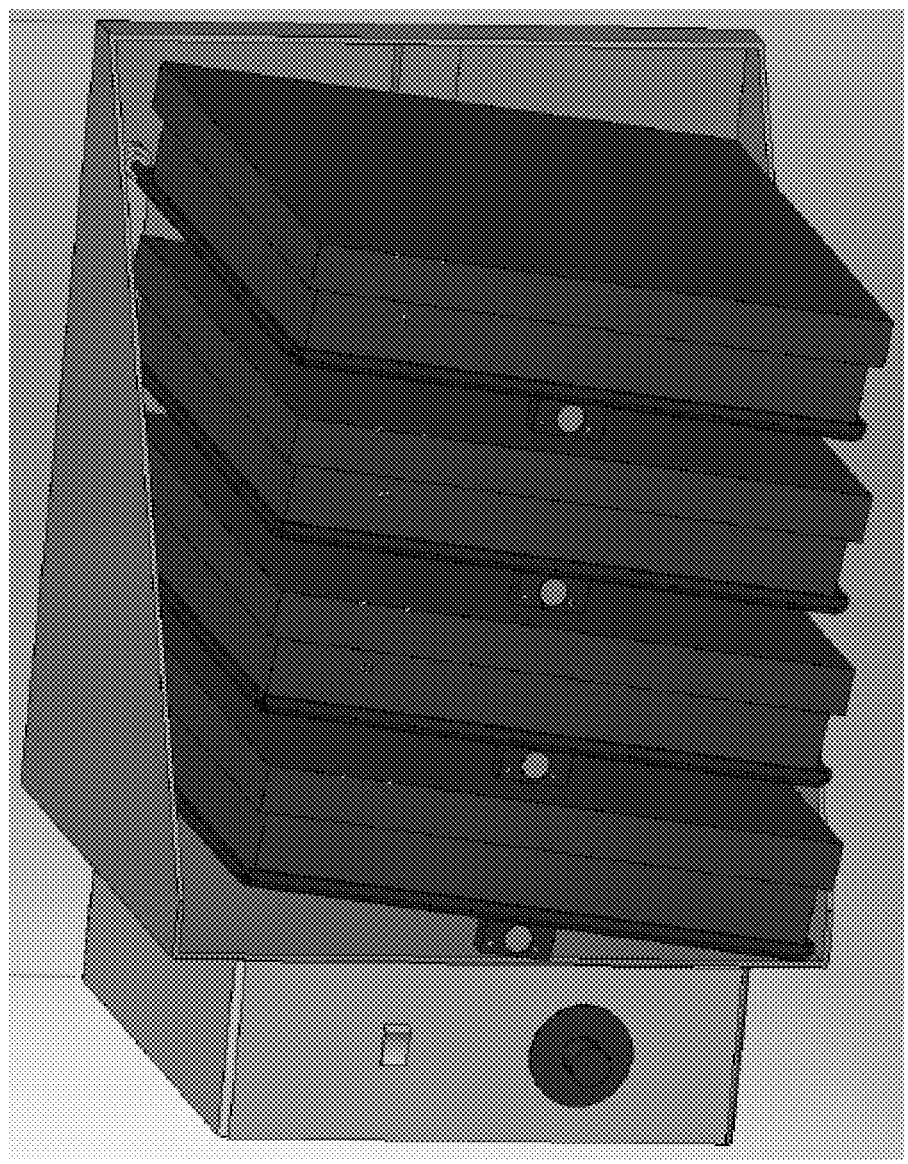

FIG. 4a shows a rocker reservoir for spheroid formation. FIG. 4b shows a multi-shelf rocker for large-scale spheroid formation. The multi-shelf rocker can rock at 5-20 cycles/min. The multi-shelf design can allow for proper rocking of all boxes (as opposed to stacking boxes on a single shelf rocker). Rocker boxes can have a silicone rubber membrane with gas inflow/outflow circuit underneath (72-75% Nitrogen+21% $O_2$, 4-7% $CO_2$—$CO_2$ can be used to maintain pH within a physiologic range). Oxygenation and pH of the media during spheroid formation can be determined by the gas inlet conditions. One purpose of the multi-shelf rocker can be large-scale production of spheroids from freshly isolated or cryopreserved hepatocytes.

Figure 4C:
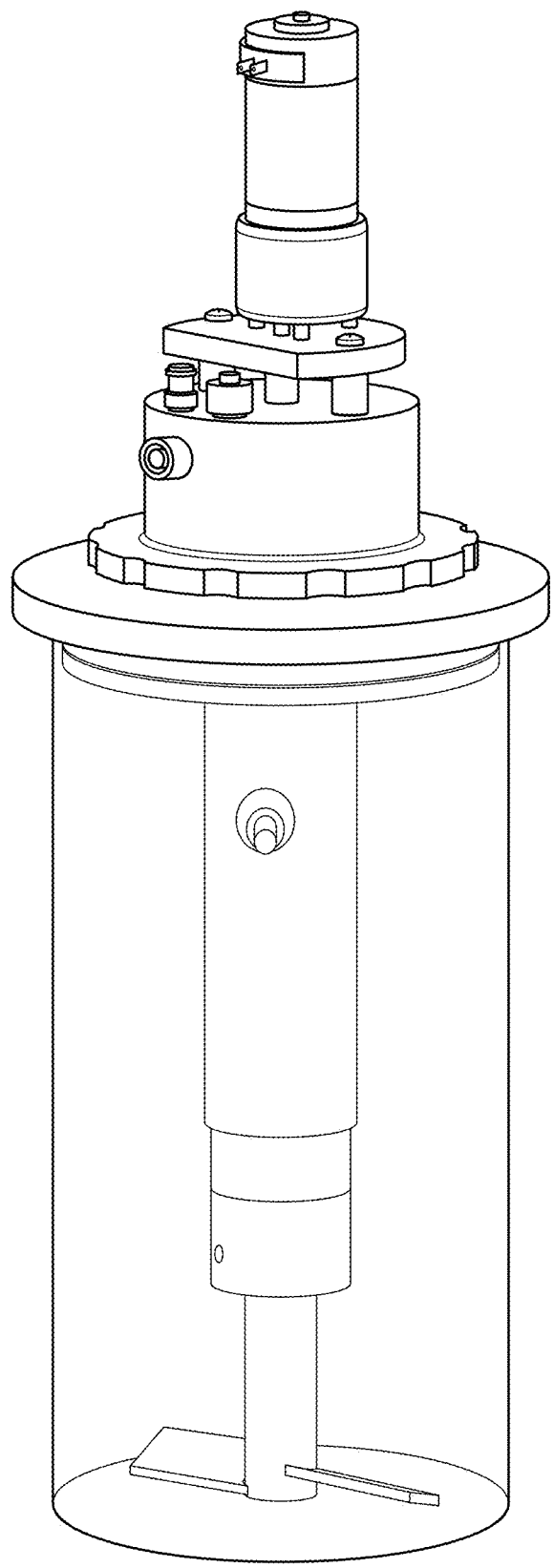
Figure 4D:
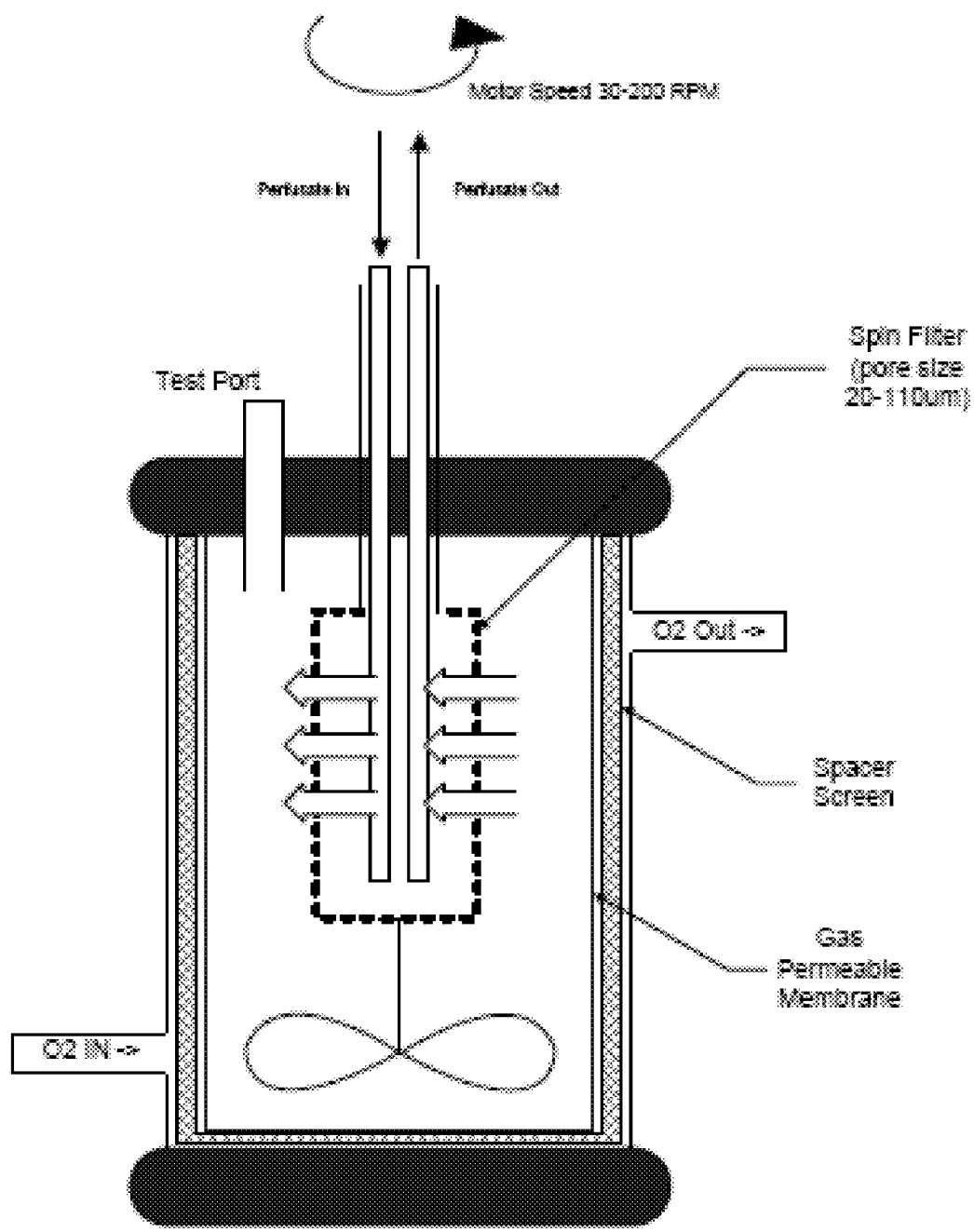

FIG. 4c shows a spinner reservoir (e.g., a 2 liter volume spinner reservoir) for extracorporeal use. FIG. 4d schematically shows the spinner reservoir of FIG. 4c. In some cases, the spinner reservoir can include a spin basket filter. The filter can rotate at about 30-200 rpm. In some cases, the filter can spin unidirectionally when in use. The filter can be designed such that bidirectional flow is allowed to unclog the filter. The pore size for the filter mesh can be between 10-100 microns. In some cases, the mesh has a pore size of 20-40 microns or smaller. In some cases, the spinner reservoir can include a silicone rubber membrane that is gas permeable. The membrane can have a large surface area for greater gas exchange which may support cell viability and biochemical activity at an increased cell density. Heparin and/or Coumadin can be used in both the spinner reservoir and the rocker reservoir at concentrations to balance anticogulation with spheroid size. In some implementations, 1 IU/mL heparin and 1 μg/mL Coumadin are used. The spinner design can serve several purposes including to maintain the spheroids in suspension and to allow continuous perfusion of the spheroid reservoir with minimal loss of spheroids from the reservoir. The cell filter inside of the spinner reservoir can be continuously cleaned of cells by the continuous inflow and outflow design of the propeller shaft. This continuous action can minimize the build up of cells on the filter, avoids plugging of the filter, and minimizes the loss of cells from the reservoir. A high velocity inflow and low velocity out flow can be achieved by adjusting the cross-sectional area of the inflow and outflow areas.

Figure 15A:
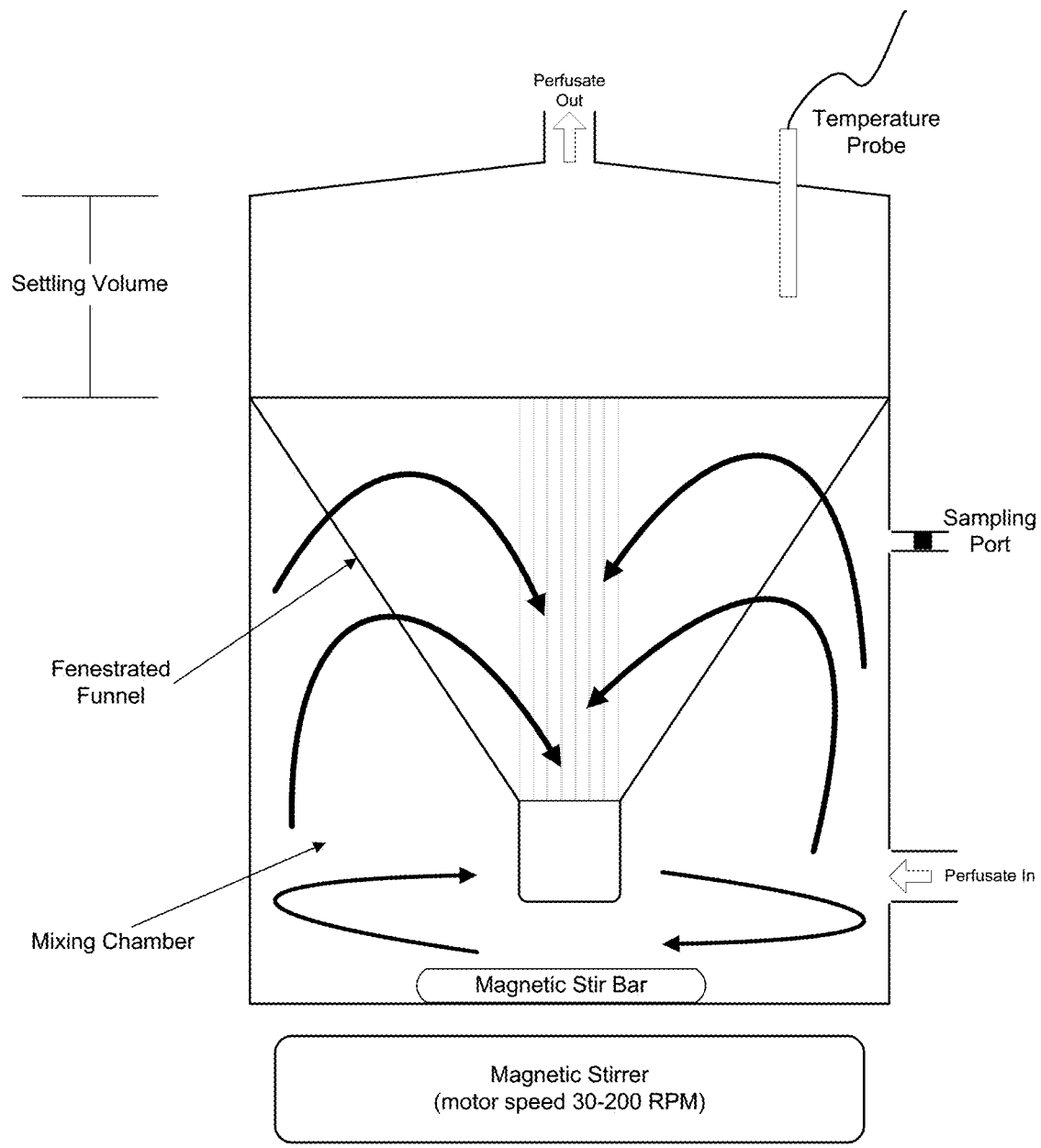
FIGS. 15(a)-15(b): Diagrammatic (a) and photographic (b) illustration of an exemplary fenestrated funnel design of a spheroid reservoir.
Figure 15B:
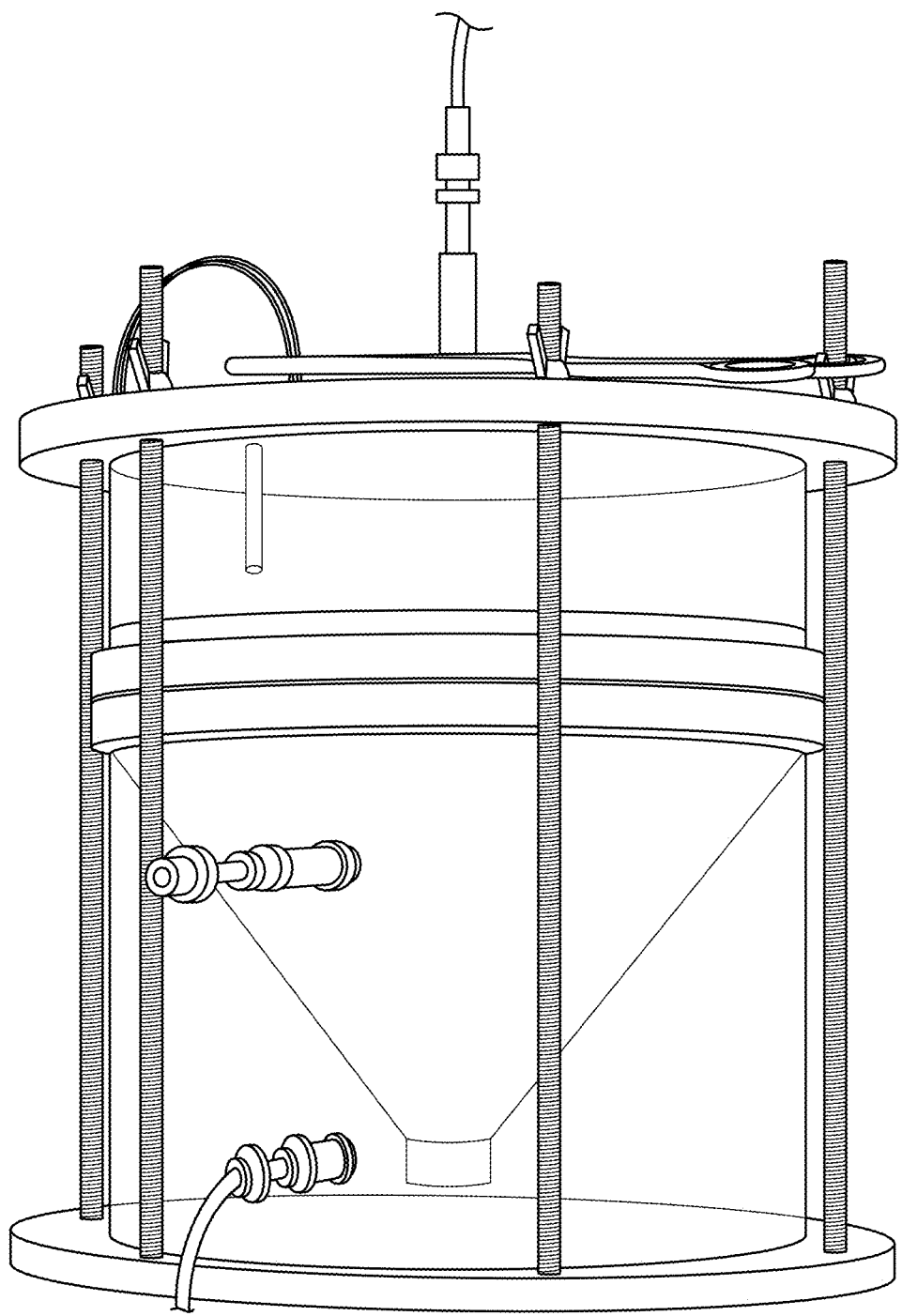

In some cases, the spheroid reservoir can be a container (e.g., a cylindrical container) having up of two compartments (e.g., a mixing chamber and a settling volume chamber) that can be separated from one another by, for example, a partition in the form of a fenestrated funnel as illustrated in FIGS. 15a and 15b. One or more stir bars can be located in the mixing chamber. For example, a stir bar can be placed at the center and base of the mixing chamber. This spinning action can create a vortex effect that pulls flow along with cells down through the spout of the funnel and thus can minimize the net loss of spheroids out of the mixing chamber. The fenestrated funnel can dampen the conversion of radial flow lines to axial flow lines and can allow the top volume of the reservoir to serve as a settling column. This dampening effect can be enhanced by a vortex that can be created as flow crosses the fenestrated funnel and is drawn down through the spout of the funnel by, for example, a centrally located stir bar at the bottom of the mixing chamber. Continuous flow can enter the reservoir at the base within the mixing chamber and can exit the reservoir through an outlet at the center and top of the container. In some cases, the reservoir can have an opening for a temperature probe and an opening for a sampling port.

A fenestrated funnel can be composed of a variety of materials such as polypropylene, polyethylene, or polycarbonate. The material can be a material that is not susceptible to cell sticking. One purpose of the fenestrated funnel can be to create a settling column in the upper volume of the reservoir while allowing a mixing chamber in the lower volume of the reservoir. Studies can be performed to identify an optimal position of the funnel spout. Locating the spout closer to the bottom of the mixing chamber can enhance the vortex effect and thus can be associated with a reduced number of particles leaving the mixing chamber and entering the settling column and exiting the reservoir through its outlet. A distance less than 5 cm from the chamber bottom can be associated with fewer particles existing, and the optimum height from the bottom can be about 1-2 cm above the bottom of the mixing chamber. Other specifications for the design of the fenestrated funnel reservoir can be as follows. The bioreactor height can be at least 24 cm tall (including the settling volume) (e.g., between 24 cm and 100 cm, between 24 and 75 cm, or between 24 and 50 cm), the fenestrated funnel itself can be between 10 and 20 cm tall (e.g. about 16.5 cm tall), the angle of the funnel can be between about 50° and 70° (e.g., about 60°), the spout diameter can be between about 0.5 and 2 cm (e.g., about 1.25 cm of at least about 1 cm in some cases), the fenestrations can be between about 1 to 4 mm wide (e.g., at least 1 mm wide), the funnel geometry can be determined such that the area of the windowed openings are about equal to the cross-sectional area of the settling column, and the percent open area of the fenestrated funnel can be no less than about 50 percent.

As described herein, a variety of studies were conducted using microbeads and spheroids made from rat and pig hepatocytes. These studies demonstrate that the settling column effect is able to separate spheroids measuring 60 microns or greater at a settling velocity of 1-2 cm/min (0.018 to 0.034 cm/sec). Based on these flow parameters, the spheroid reservoir can be operated at a flow rate of 400 mL/min if its cylindrical inner diameter is 7 inches (approximately 180 mm). Naturally, the optimal conditions for the system may be influenced by the number of spheroids in the reservoir and the diameter of these spheroids since larger spheroids have a faster settling rate and could tolerate a higher axial velocity within the settling column.

When using the design of the fenestrated funnel bioreactor, a stirring rate range of 30 to 200 RPM can be used. The contents can be well mixed without overly agitating the settling volume. The stir bar length can be between 2 and 15 cm (e.g., 8 cm). The overall bioreactor can be cylindrical in shape. The stir bar and funnel can be axially aligned with the center axis of the cylindrical bioreactor. The flow rate can be 100 to 400 mL/min with 400 mL/min being optimal based on human liver function. The device can have a single inlet and a single outlet. A test or sampling port can be provided into the mixing chamber. In some cases, a temperature probe port can be provided. A 1 µm filter (or smaller) can be included in the Bio-Artificial Liver circuit on the outlet of the bioreactor. This filter could be incorporated into the bioreactor by locating it between the settling column and the outlet. The bioreactor must be made from biocompatible materials (USP class 6). A 1 um filter (or smaller) is included in the bio-artificial liver circuit on the outlet of the bioreactor. This filter could be incorporated into the bioreactor by locating it between the settling column and the outlet. A 1 um filter (or smaller) is included in the SRBAL circuit on the outlet of the bioreactor. This filter can be incorporated into the bioreactor by locating it between the settling column and the outlet.

In some cases, the spheroid reservoir (e.g., the spheroid reservoir having a fenestrated funnel) can be made primarily from acrylic using standard machining operations. The funnel can be made from ABS using a fluid deposition modeling rapid prototyping process. The entire device can be made using plastic molding processes (e.g., injection and/or blow molds).

Figure 16:
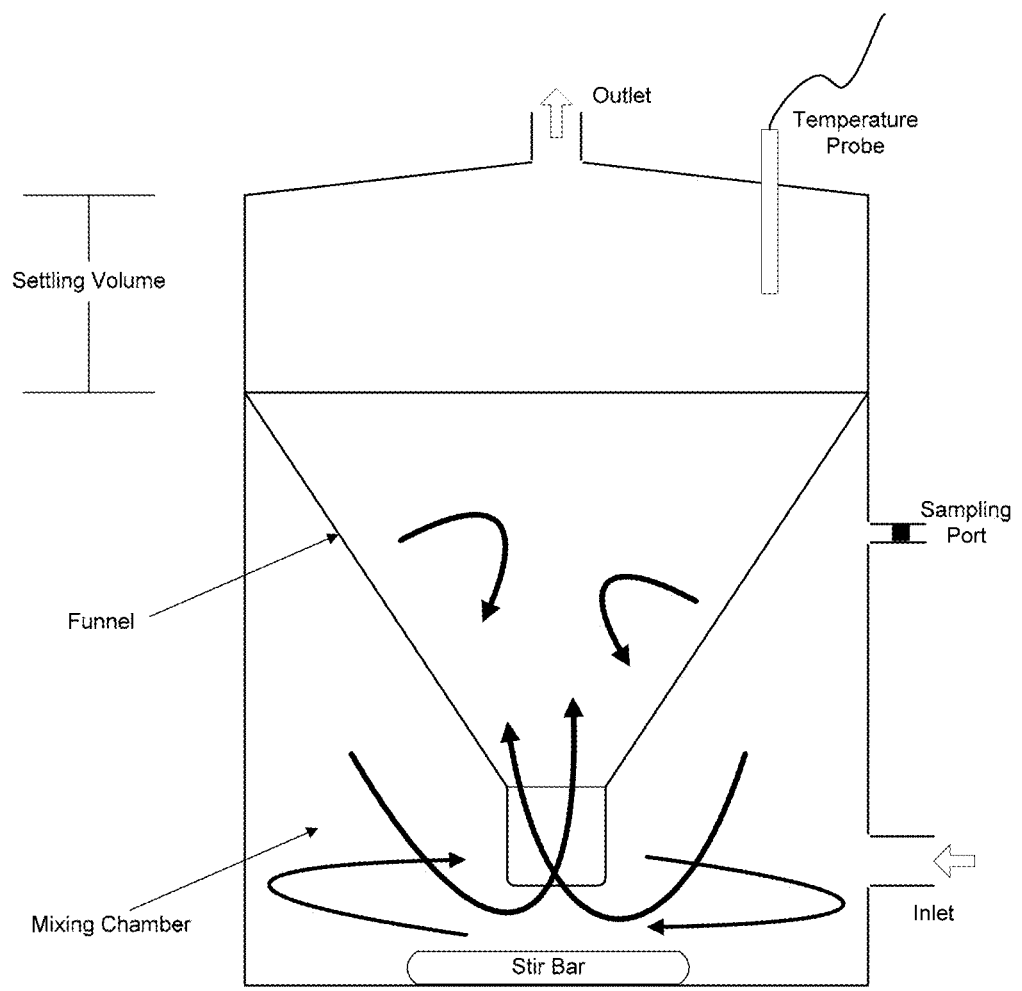
FIG. 16: Diagrammatic illustration of an exemplary plain funnel design of a spheroid reservoir.
Figure 17:
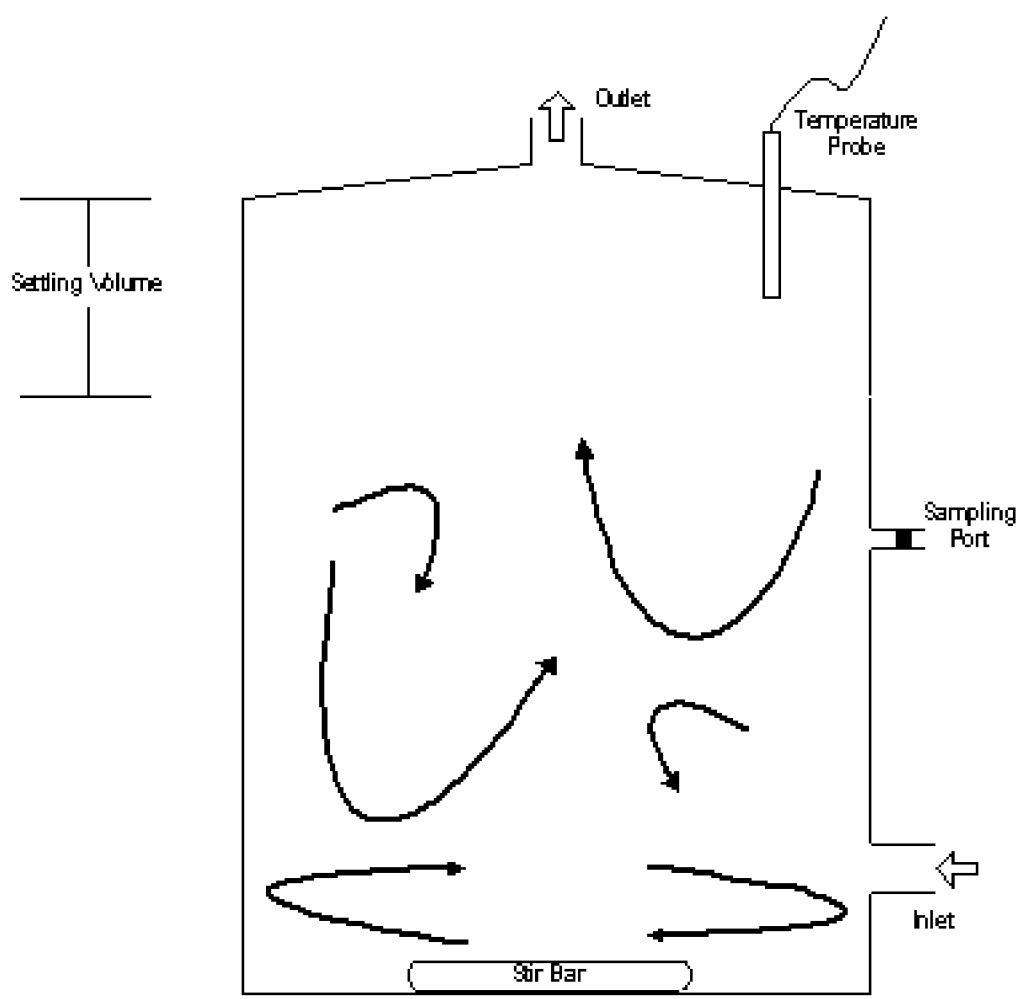
FIG. 17: Diagrammatic illustration of an exemplary straight settling column design of a spheroid reservoir.

In some cases, a spheroid reservoir can be of a SRBAL device provided herein can have a design as shown in FIG. 16 or 17.

A SRBAL device provided herein can provide liver detoxification to patients in liver failure. Detoxification can be provided by metabolically active hepatocytes (e.g., primary porcine hepatocytes) within the spheroid reservoir, as well as the charcoal column and resin column within the albumin perfusate. Metabolic activity of hepatocytes in the spheroid reservoir can be assessed by cell viability, oxygen consumption, albumin production, and P450 activity of the primary hepatocytes via a sample port in the reservoir. The device can be designed to function extracorporeally (e.g., at the bedside of the patient with acute liver failure (ALF)). The device may serve as an alternative to liver transplantation in the possibility of spontaneous recovery of liver failure or as a bridge to liver transplantation if liver failure is not reversible.

A SRBAL provided herein can provide a synergistic benefit by combining albumin dialysis with hepatocyte-based therapy. Modifications such as using fresh rather than cryopreserved hepatocytes, increasing the dose of hepatocytes from 70 grams to either 200 grams or 400 grams, lengthening the duration of therapy to continuous perfusion, along with added benefits of albumin dialysis, may also make BAL therapy efficacious in ALF. The SRBAL can also detoxify ammonia. One way to increase ammonia detoxification is by enhancing the transcription factors that regulate ureagenesis gene expression, such as HNF6. In some cases, the SRBAL therapy can have two-fold benefits by both providing essential hepatocellular functions, such as detoxification of ammonia to urea, while also reducing the SIRS response to acute liver injury.

The invention will be further described in the following examples, which do not limit the scope of the invention described in the claims.

EXAMPLES

Example 1: The SRBAL Improves Survival and Reduces Extrahepatic Manifestations in a Canine Model of D-Galactosamine-Induced FHF Testing of the SRBAL was conducted on six dogs (15-20 kg wt.) under three treatment conditions: Fresh Hepatocyte SRBAL ($2\times10^{10}$ fresh pig hepatocytes), No Cell BAL (control), and No BAL (control). After induction of isoflurane anesthesia, four probes were placed in the dog brain to measure ICP, microdialysis fluid, temperature, and tissue oximetry. Dogs received D-galactosamine (2.0 g/kg) at t=0 hr; BAL therapy was initiated at t=24 hr. Dogs received a 5 mmole bolus of $NH_4Cl$ on day 1 (t=6 hr) and three 5 millimole boluses of $NH_4Cl$ at t=28 hr, t=32 hr, t=36 hr to assess detoxification of $NH_3$ before and after onset of liver failure. Arterial $NH_3$ samples were obtained immediately before and 60 minutes after $NH_4Cl$ boluses. It was observed that dogs treated with the hepatocyte SRBAL group maintained normal intracranial pressures and survived the experimental period, while all control animals developed intracranial hypertension and died from brain herniation (Table 1).

TABLE 1

Summary Table -
Preliminary Studies of SRBAL as Treatment of ALF Dogs

| Endpoint | Units | Fresh Hepatocyte BAL n = 2 | No Cell BAL - Control n = 2 | No BAL - Control n = 2 |
|---|---|---|---|---|
| Survival | hr | EOT* | 35, 41 | 36, 40 |
| ALT (peak) | U/L | 6020, 8040 | 6520, 7300 | 8090, 7003 |
| ICP (final peak) | mmHg | 20, 23 | 56, 69 | 55,** |
| $NH_3$ (peak blood level) | µmol/L | 45, 65 | 101, 272 | 131, 179 |
| Brain Glucose (final) | mmol/L | 5.2, 9.3 | 0.23, 0.42 | 0.34,** |
| Brain Lactate (final) | mmol/L | 2.8, 1.5 | 2.3, 8.9 | 5.8,** |
| Brain Glycerol (final) | umol/L | 26.5, 39.4 | 117.2, 163.4 | 206.6,** |

*end of therapy
**intracranial probes not placed

Improved outcome in the hepatocyte treatment group occurred in the setting of similar liver injury, based on peak serum ALT levels, in all three groups. Herniation was associated with a sudden decline in brain tissue oxygenation (<10 mmHg) and reduced cerebral blood flow. Brain glucose declined and brain lactate increased in control animals reflecting cerebral ischemia with herniation. The marked rise in brain glycerol observed in control animals at the time of herniation was further evidence of acute neuronal damage and was diagnostic of brain death. In contrast, final brain levels of glucose, lactate, and glycerol were normal in dogs treated with fresh hepatocytes in the SRBAL.

An added benefit of treatment with the SRBAL was improved detoxification of $NH_3$. In fact, the response of ALF dogs to a 5 millimole bolus of $NH_4Cl$ during SRBAL treatment was similar to their response on day 1 before onset of ALF (0.47±0.81 vs. 0.34±0.63 umol/L/mmol, p=NS). In contrast, the response of ALF dogs in the No Cell BAL group to the same 5 millimole bolus of $NH_4Cl$ was significantly elevated from baseline (3.47±1.77 vs. 0.63±0.34 µmol/L/mmol, p=0.025). Improved ammonia detoxification by the SRBAL was associated with high viability of porcine hepatocyte spheroids at the end of BAL therapy (viability >90%). Oxygen consumption by hepatocyte spheroids in the SRBAL also remained stable, ranging from 0.94 to 0.88 mmol $O_2$/hr from start to end of extracorporeal therapy.

Example 2: Treatment of ALF Dogs with the Hepatocyte SRBAL Contributes to Sustained Normalization of the Systemic Inflammatory Response Syndrome (SIRS)

Figure 5A:
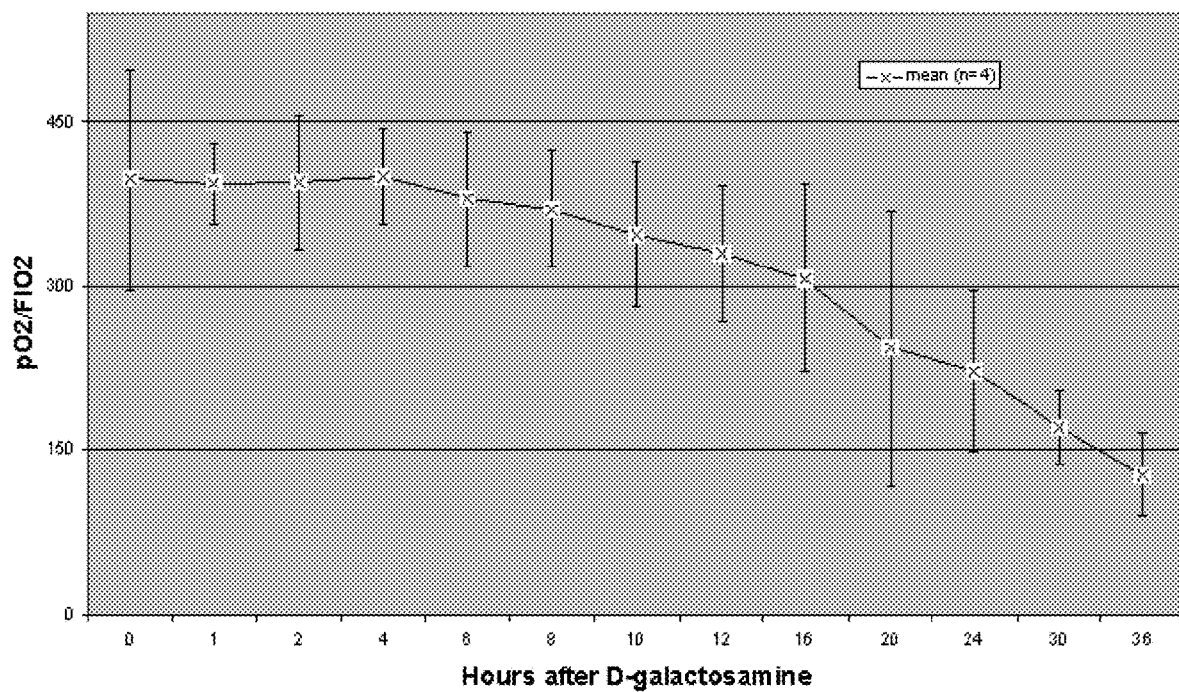
FIGS. 5(a)-5(c): Systemic Inflammatory Response Syndrome (SIRS) of D-Gal-Induced ALF is associated with extrahepatic organ dysfunction—including respiratory failure as shown in (a). Using serum TNFα as a marker of SIRS, the SIRS response of ALF was normalized by treatment with the Hepatocyte SRBAL (b). Clearance of LPS by Kupffer cells of the liver was suggested by the gradient between LPS levels sampled in blood from the portal vein and hepatic vein (c). The rise in TNFα activity after D-Gal in dogs could not be explained fully by a short transient release of LPS from the gut, suggesting the existence of other initiators of SIRS in non-infectious acute liver failure.
Figure 5B:
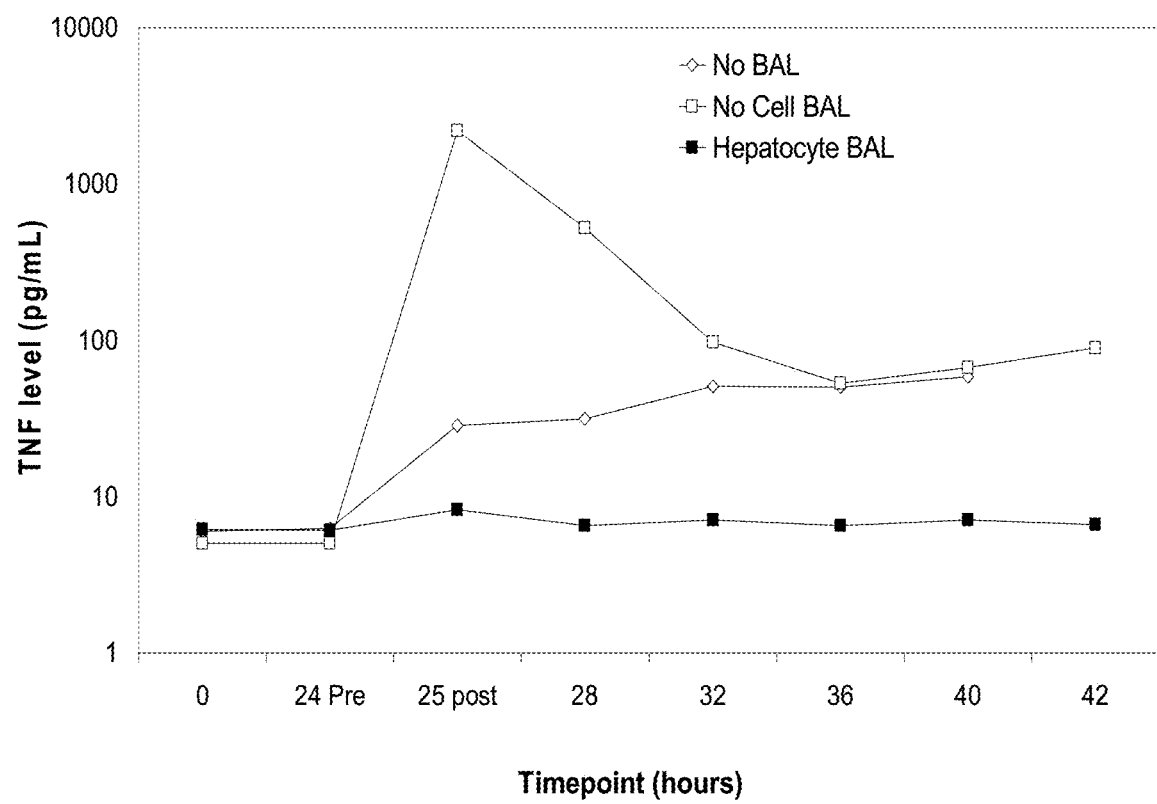
Figure 5C:
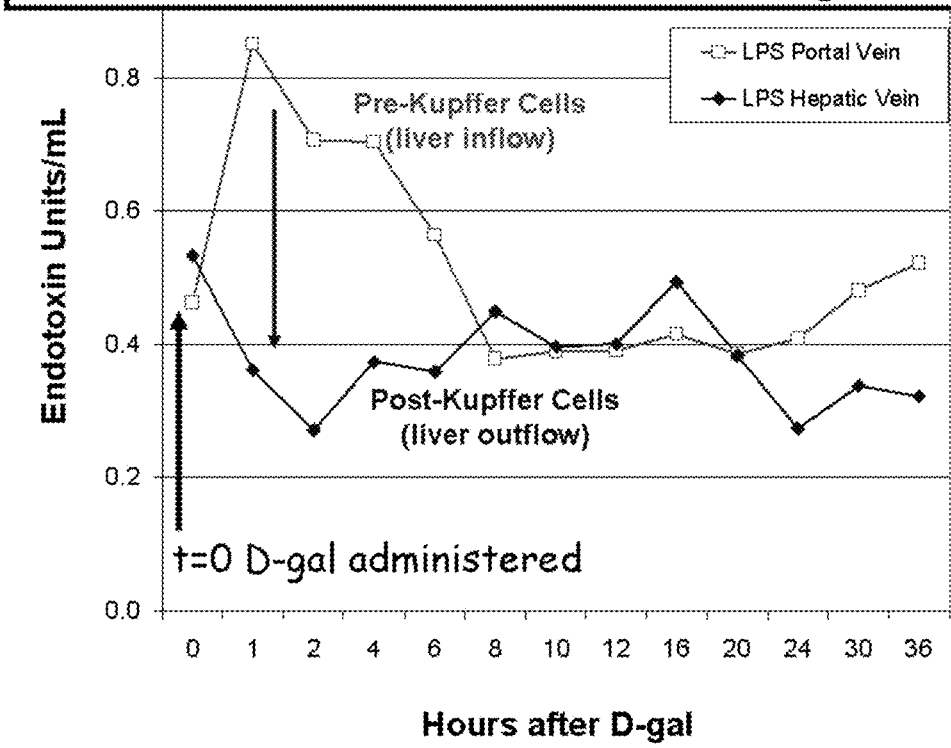

Treatment of ALF dogs with the hepatocyte SRBAL was associated with sustained normalization of the systemic inflammatory response syndrome (SIRS). Hallmarks of SIRS such as hypotension, oliguria, and respiratory dysfunction (FIG. 5a) were observed in control dogs beginning 12 hours after administration of D-galactosamine. A rise in blood levels of TNFα was observed in control dogs at 24 hours post D-galactosamine. Blood levels of TNFα rose steadily until expiration in the no BAL group. A sharp rise in TNFα was observed at the initiation of No cell BAL therapy and remained elevated in the range of the No BAL group up until brain death. In contrast, normal levels of TNFα were measured in both dogs treated by the hepatocyte SRBAL (FIG. 5b). These results indicate that liver cells improve biocompatibility of the SRBAL and reduce the SIRS response of D-gal-induced ALF. The SIRS response of ALF was associated with a transient rise in LPS levels in the portal vein but not hepatic vein (FIG. 5c), suggesting clearance of LPS by cells, such as Kupffer cells, in the liver. However, this short burst in LPS could not fully explain the sustained SIRS response observed after administration of hepatotoxin. These studies suggest the existence of other mediators of SIRS of ALF besides LPS. Mechanistic studies are conducted to identify endogenous mediators of the SIRS of ALF which may be cleared during SRBAL therapy such as degradation productions of the extracellular matrix.

Figure 6A:
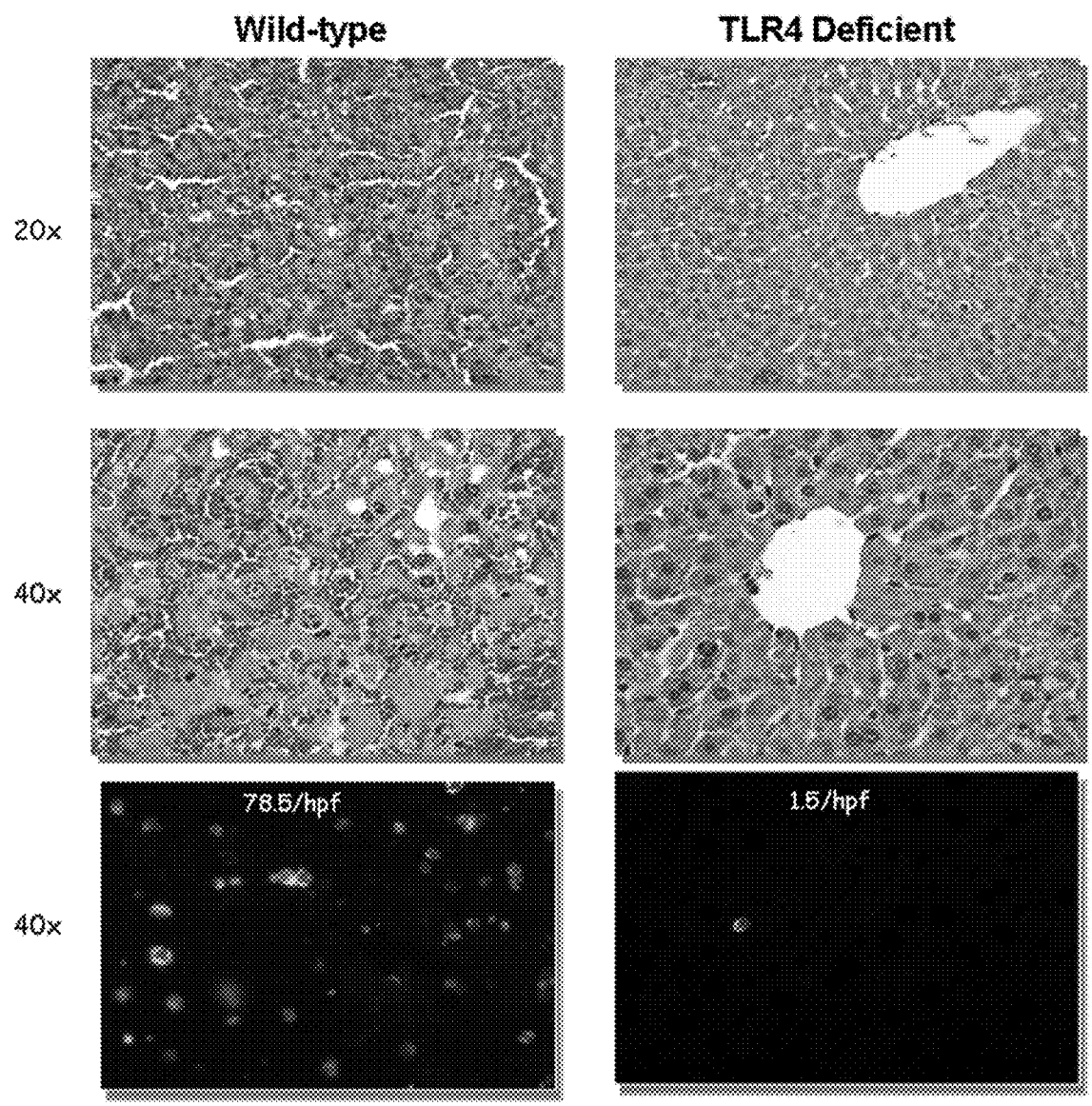

Example 3: Functional TLR4 Signaling Assists in the Development of Liver Pathology and SIRS after Toxic Exposure to Acetaminophen or D-Gal/LPS The role of TLR4 in ALF and SIRS was studied. FIG. 6a shows that TLR4 deficient (mutant) mice are protected from Dgal/LPS induced liver injury while wild-type mice develop severe necrosis of their liver with extensive TUNEL(+) apoptosis after exposure to Dgal/LPS. A similar protective effect of TLR4 deficiency was also observed when wild-type and TLR4 mutant mice were treated with acetaminophen (APAP) at 500 mg/kg—a dose which is highly toxic with 100% mortality in wild-type mice (Table 2). Systemic inflammation was confirmed in wild-type mice after both APAP and Dgal/LPS by rising blood levels of TNFα and neutrophil infiltration in their lungs at necropsy. In contrast, lung histology and systemic levels of TNFα remained normal in TLR4 deficient mice. FIG. 6b suggests that hepatocyte death and the SIRS response to toxin-induced liver injury is mediated by TLR4 expressed on Kupffer cells. TLR4 deficient Kupffer cells may also explain the protective effects observed in TLR4 deficient mice after toxin exposure (FIG. 6c). Consistent with this observation, a significant reduction in the toxicity of Dgal/LPS was observed in wild-type mice pretreated with gadolinium chloride (Table 2). Pretreatment with gadolinium chloride reduced the number of Kupffer cells in the liver by 48% (31±6 to 16±4 cells/HPF, p<0.001), and lowered peak ALT levels from 2458±2347 U/mL to 278±196 U/mL.

TABLE 2

Summary Table of Liver Injury
TLR4 + (Wild type) vs. TLR4 - (Deficient)

| Condition | ALT (U/mL) | | TUNEL (+cells/HPF) | |
|---|---|---|---|---|
| (n = 10/group) | TLR4 + | TLR4 - | TLR4 + | TLR4 - |
| APAP (18 hr) | 9054 ± 4793 | 4810 ± 4045* | — | — |
| DGal/LPS (6 hr) | 2458 ± 2347 | 125 ± 131** | 177 ± 45 | 88 ± 41* |
| DGal/LPS/ Gadolinium (6 hr) | 278 ± 196 | 196 ± 127 | — | — |
| LPS alone (6 hr) | 153 ± 69 | 46 ± 16* | 4 ± 2 | <1* |
| DGal alone (6 hr) | 43 ± 9 | 54 ± 18 | <1 | <1 |
| Saline (6 hr) | 27 ± 28 | 31 ± 14 | <1 | <1 |

*p value <0.05 (vs. wild type, same condition)
**p value <0.001 (vs. wild type, same condition)

Figure 7C:
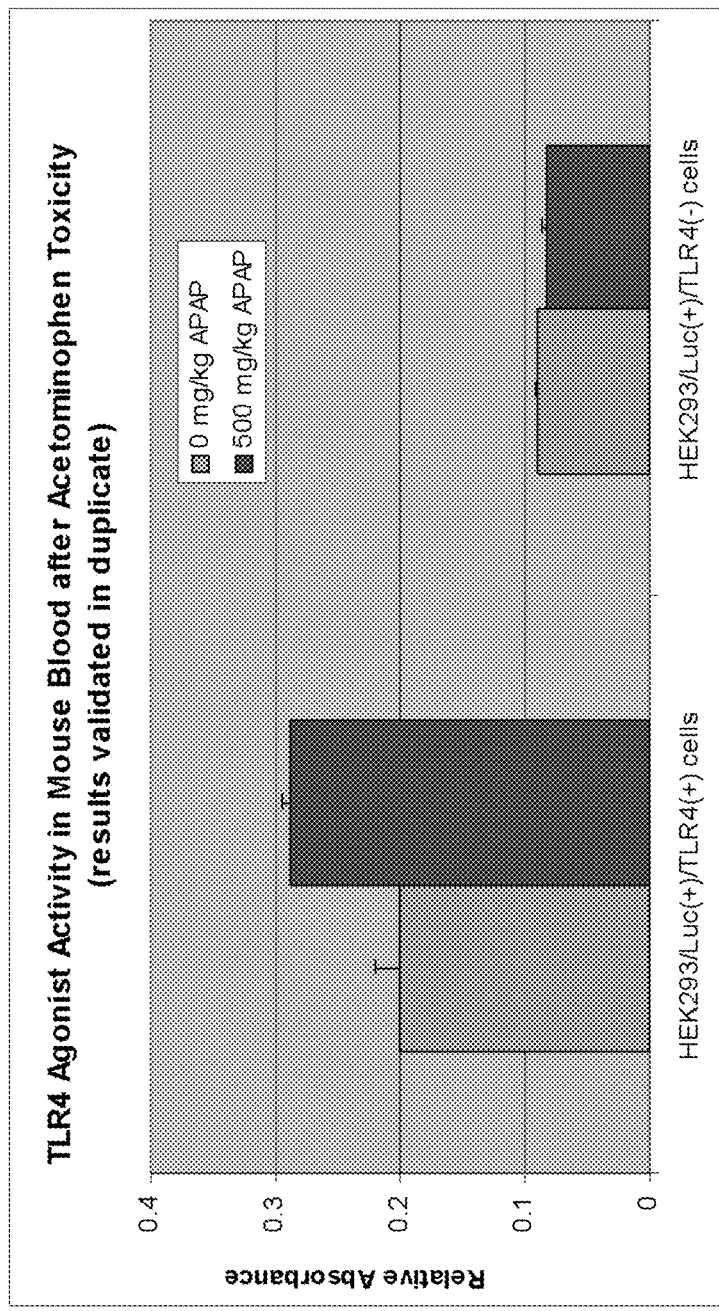

Further evidence supporting TLR4 as a signaling molecule in the SIRS response to ALF is illustrated in FIG. 7. FIGS. 7a-b show the assay, as well as the TLR4 receptor complex, used in the study. FIG. 7c demonstrates that serum obtained from critically ill mice, 6 hours after APAP 500 mg/kg, contains high levels of TLR4 agonist activity compared to 0 mg/kg sham controls (p<0.001).

Figure 8:
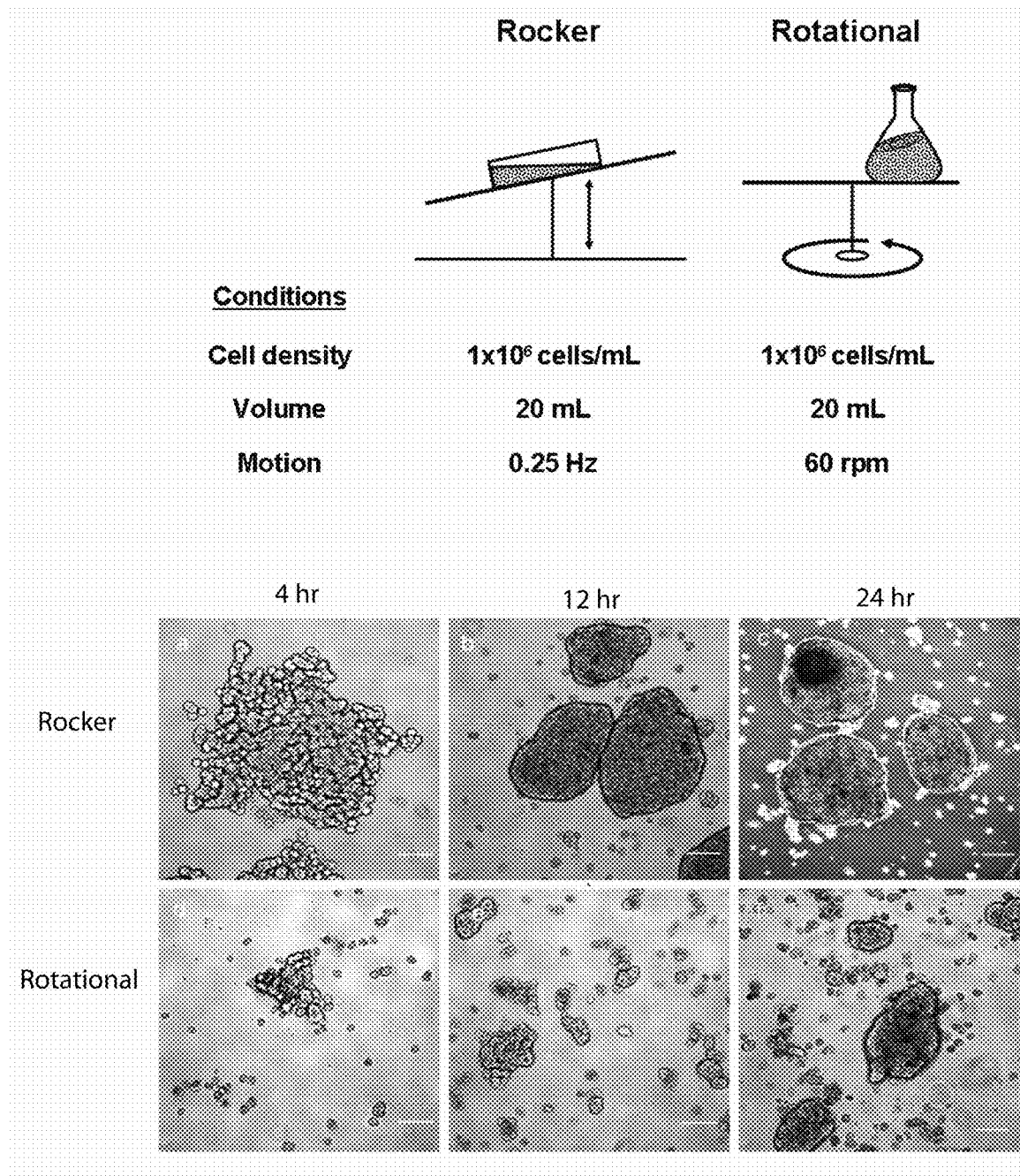
FIG. 8: Comparison of rocked vs. rotational conditions (upper panel) along with hepatocyte spheroids viewed by phase microscopy during spheroid formation (lower panel). Hepatocytes ($1 \times 10^6$ cells/mL) were rocked at 0.25 Hz or rotated at 60 rpm to induce spheroid formation. Representative images of spheroid formation by rocked technique are provided at 4 hr, 12 hr, and 24 hr and by rotational technique at 4 hr, 12 hr, and 24 hr. Scale bars equal 50 μm.

Example 4: To Determine the Optimal Operating Conditions of the SRBAL Based on a Bioengineering Analysis of Factors Influencing Spheroid Formation, Biochemical Performance, Mass Transfer Across the BAL Membrane, and Membrane Biocompatibility 1. Regulation of Spheroid Formation to Improve Biochemical Performance of the SRBAL In order to determine whether spheroid formation could be regulated to improve biochemical performance of the SRBAL, spheroid formation by traditional rotational technique and by a rocker technique described in U.S. Pat. No. 25,160,719 were first compared. Several advantages of the rocker technique over the rotational technique were observed. These advantages include a much faster rate of spheroid formation, better control of spheroid size, and greater percent of hepatocytes incorporation into spheroid aggregates by the rocker technique. After 24 hours of rocking, most (85%) of inoculated hepatocytes had incorporated into well-formed spheroids of greater than 40 µm in diameter (FIG. 8).

Figure 9:
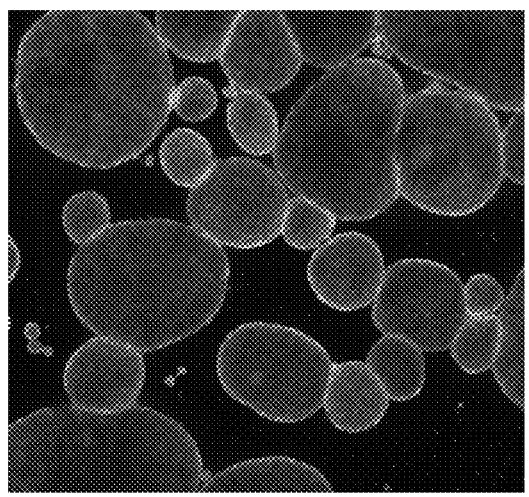
FIGS. 9(a)-9(c): Representative hepatocyte spheroids stained by Fluoroquench™ after 5 days in rocked culture. Viable cells stained green while dead cells stained red. (a) low power of spheroids; (b) single spheroid demonstrating numerous viable cells by FITC filter; (c) same spheroid with a small focus of 2-3 dead cells by rhodamine (red) filter.
Figure 9:
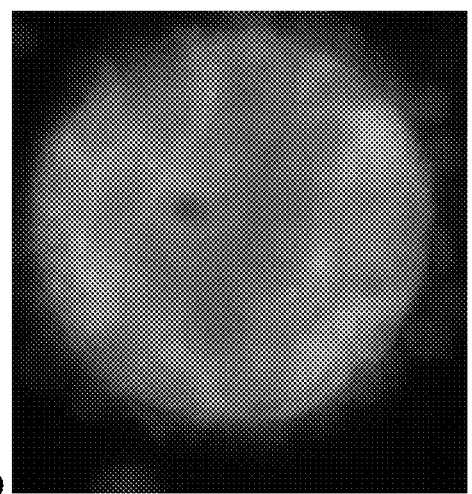
Figure 9:
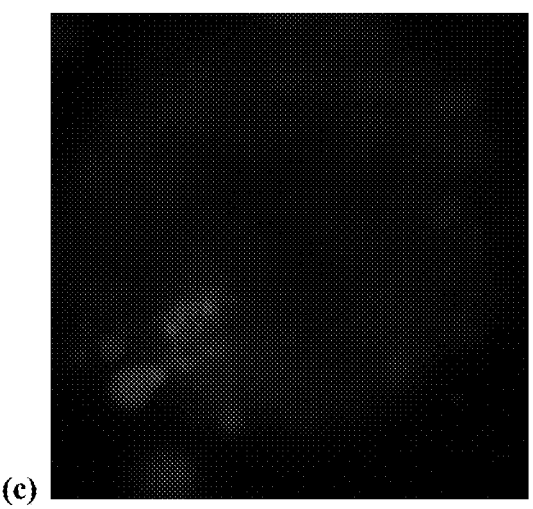

At 48 hours, only 13% of cell particles measured less than 40 µm in diameter by Coulter counter measurement. The majority of rocker-formed aggregates (84%) ranged in diameter of 75-200 µm. In contrast, only 58% of hepatocytes were incorporated into spheroids under rotational conditions at 24 hours. Most unattached hepatocytes appeared dead. Spheroid formation provided a protective benefit as greater than 95% of all hepatocytes present in spheroids were viable at each time point up to 14 days (FIG. 9). Improved kinetics of spheroid formation and stable spheroid integrity by rocked technique may be associated with greater biochemical performance of spheroid hepatocytes compared to monolayer controls.

Figure 10:
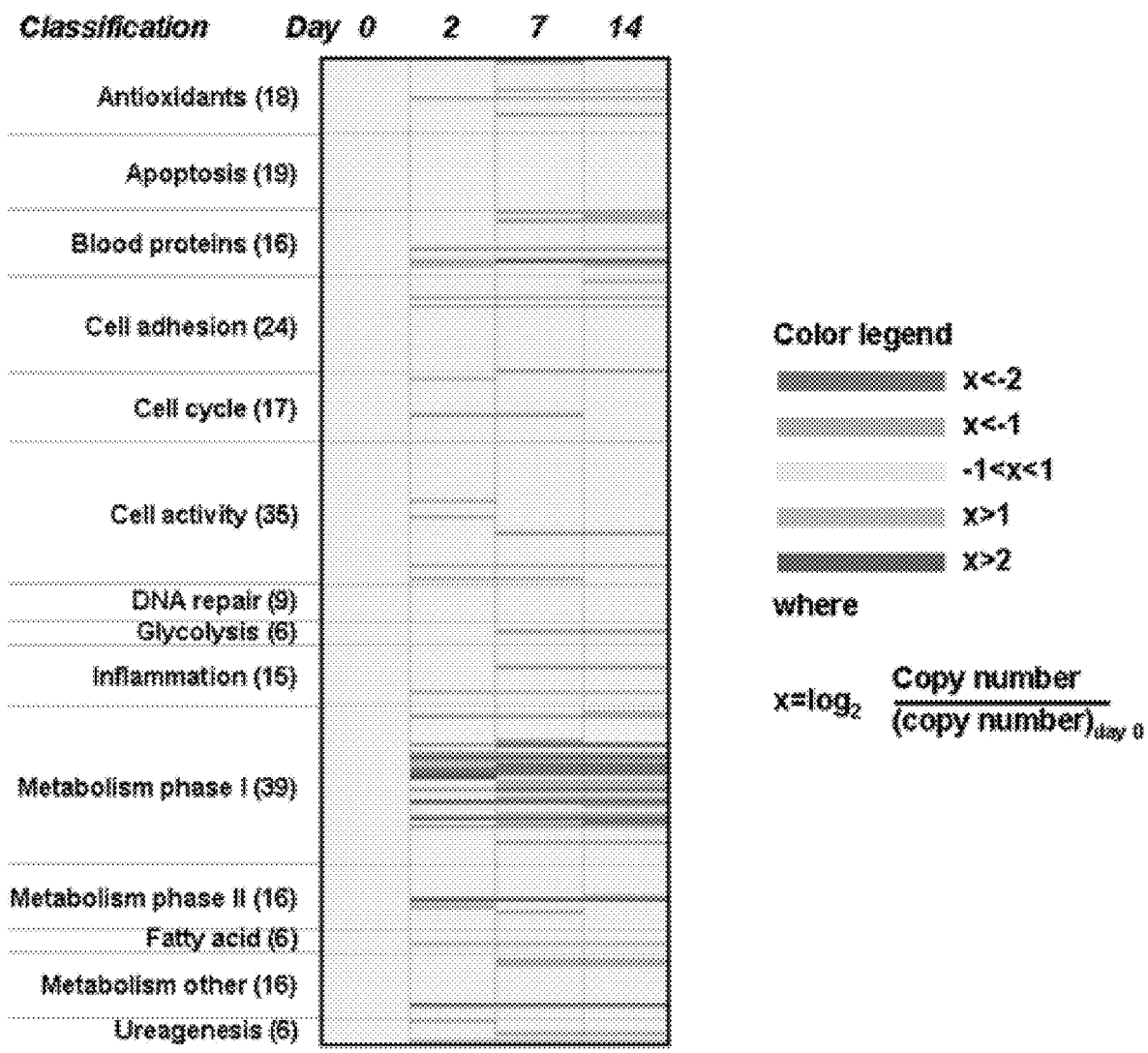
FIG. 10: Expression of 242 liver specific genes by a microarray in rocked spheroid culture over 14 days. Average expression of over 80% of these genes was stable over time (green color). A reduction in gene expression from baseline (freshly isolated rat hepatocytes) is indicated in pink or red, while an increase in expression is labeled blue.

Gene expression of rat hepatocytes over 14 days of rocked spheroid culture was profiled. A custom microarray of 242 liver-related genes was developed for this task. It was observed that the expression of 85% of these genes remained stable—less than a 2-fold increase or 50% decrease in expression—over 14 days in culture (FIG. 10). Expression increased 2-fold or greater in 5% of genes; and decreased 50% in 10% of genes. Biochemical activity of rocked spheroid hepatocytes was also superior to spheroids formed by rotational technique and to hepatocytes cultured as monolayers. These results suggest that spheroid formation can be regulated to improve biochemical performance of the SRBAL. Conditions for better spheroid formation include serum free medium supplemented with insulin/transferrin/selenium at a rocker frequency of 15 cycles per minute, and a seeding density of $5 \times 10^6$ viable hepatocytes per mL. Following 24 hours of rocking, newly formed spheroids can be concentrated to a density of $1-2 \times 10^7$ cells/mL if placed in the SRBAL with continuous oxygenation and supplementation with fresh medium.

Figure 11:
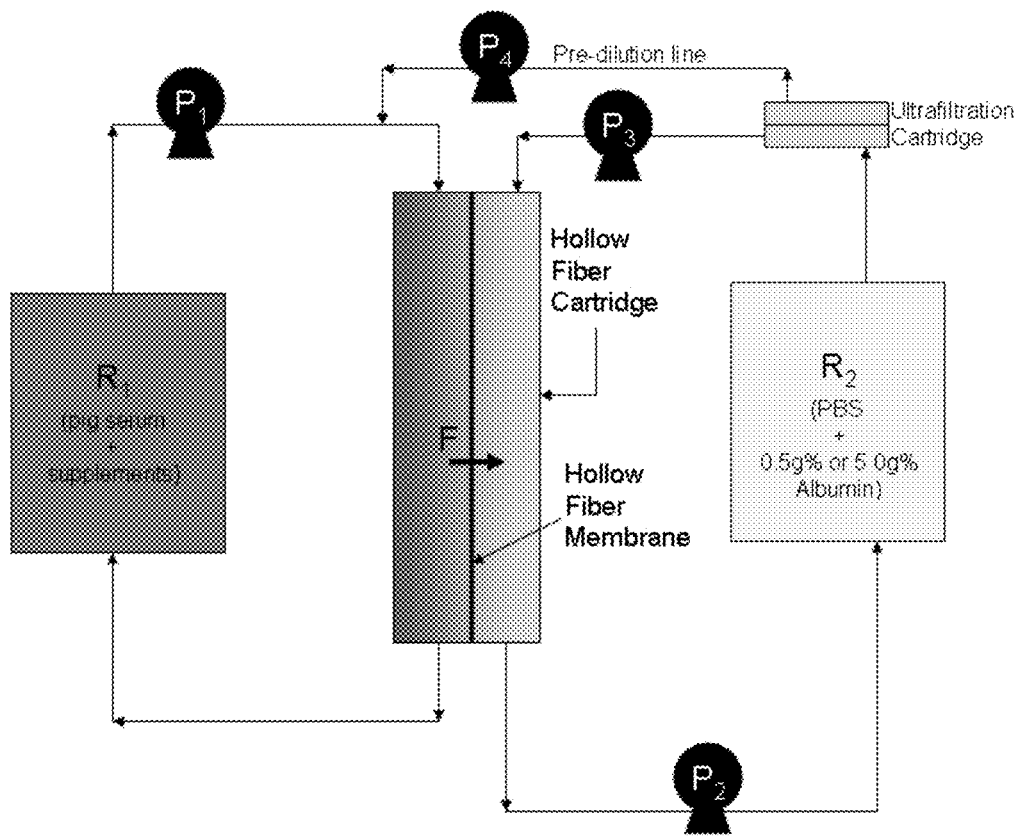
FIG. 11: Schematic of bench-top apparatus used for testing flow conditions, medium conditions, and hollow fiber membranes under optimization studies. Under diffusion conditions pumps were set so that F=0 mL/min (P1=P2=P3=100 mL/min). Pumps were set so that F=5 mL/min, 25 ml/min, or 50 mL/min under conditions of low, medium and high convective flux, respectively.

2. Influence of Flow Conditions in its Extracapillary Space on Biochemical Performance of the SRBAL The influence of flow conditions on performance of the SRBAL was studied using a four-pump bench-top apparatus as illustrated in FIG. 11. Variables considered in the optimization studies included hollow fiber membrane pore size (70 kD, 150 kD, 400 kD), pump configuration (F=0, 5, 25, 50 mL/min), and albumin concentration in R2 (0.5 g %, 5.0 g %). These three variables accounted for a total of 24 conditions that were tested using three waste molecules (ammonia, conjugated & unconjugated birubin), pig albumin, and three immune molecules (TNFα, IgG, and IgM) as markers of permeability. In all studies, Reservoir #1 was initially filled with pig plasma supplemented with each of these compounds. Reservoir #2 was primed with PBS supplemented with either 0.5 g % or 5.0 g % bovine albumin. Tubing and cartridges were primed with solutions corresponding to their side of the hollow fiber membrane. In addition, sieving coefficients of all membranes were determined by a standardized membrane technique using dextran polymers before and after permeability testing. A rank sum analysis of all 24 conditions and 8 measures of permeability was performed to determine the best condition for operation of the SRBAL in the pre-clinical efficacy studies. The rank sum analysis determined that mass transfer of albumin (p<0.001), TNFα (p<0.001) and unconjugated bilirubin (p<0.01) was greatest under high flux using either 150 kD or 400 kD membrane. When permeability of IgG and IgM was also considered, the 150 kD membrane was considered superior due to its lower permeability to these potentially harmful antibodies.

3. Influence of the Concentration of Albumin in the BAL Medium on Elimination of Polar and Non-Polar Toxins from the Patient Compartment The influence of albumin concentration in the BAL medium (R2) on elimination of polar (ammonia, conjugated bilirubin) and non-polar (unconjugated bilirubin) toxins from the patient compartment (R1) were tested using the bench-top apparatus in FIG. 11. Slightly higher rates of mass transfer were observed for all three molecules under conditions of high (5.0 g %) vs. low (0.5 g %) albumin. The studies favor use of standard albumin dialysis conditions during SRBAL therapy.

4. Influence of Permeability of the BAL Membrane on Biocompatibility, Immuno-Protection, and Biochemical Performance of the SRBAL The above studies demonstrated that mass transfer of albumin and waste molecules was greatest using the either 150 kD or 400 kD membrane. The 150 kD membrane can be used to limited transfer of larger and potentially harmful molecules of IgG and IgM into R2.

Example 5: To Establish Efficacy of the SRBAL in a Preclinical Model of ALF by Demonstrating Improved Survival and a Reversal of Hepatic Encephalopathy 1. Influence of the Dose of Freshly Isolated Porcine Hepatocytes in the Reservoir Medium on Efficacy of the SRBAL As reported in Table 1 above, studies of the SRBAL using 200 grams of fresh porcine hepatocytes demonstrated a beneficial response in the treatment of two dogs with D-gal-induced ALF. Validation studies using freshly formed spheroids or porcine hepatocytes at a dose of 200 grams or 400 grams are described in Example 8.

Example 6: Benefit of Faster or Slower Rotational Speed in Spheroid Reservoir

Figure 12A:
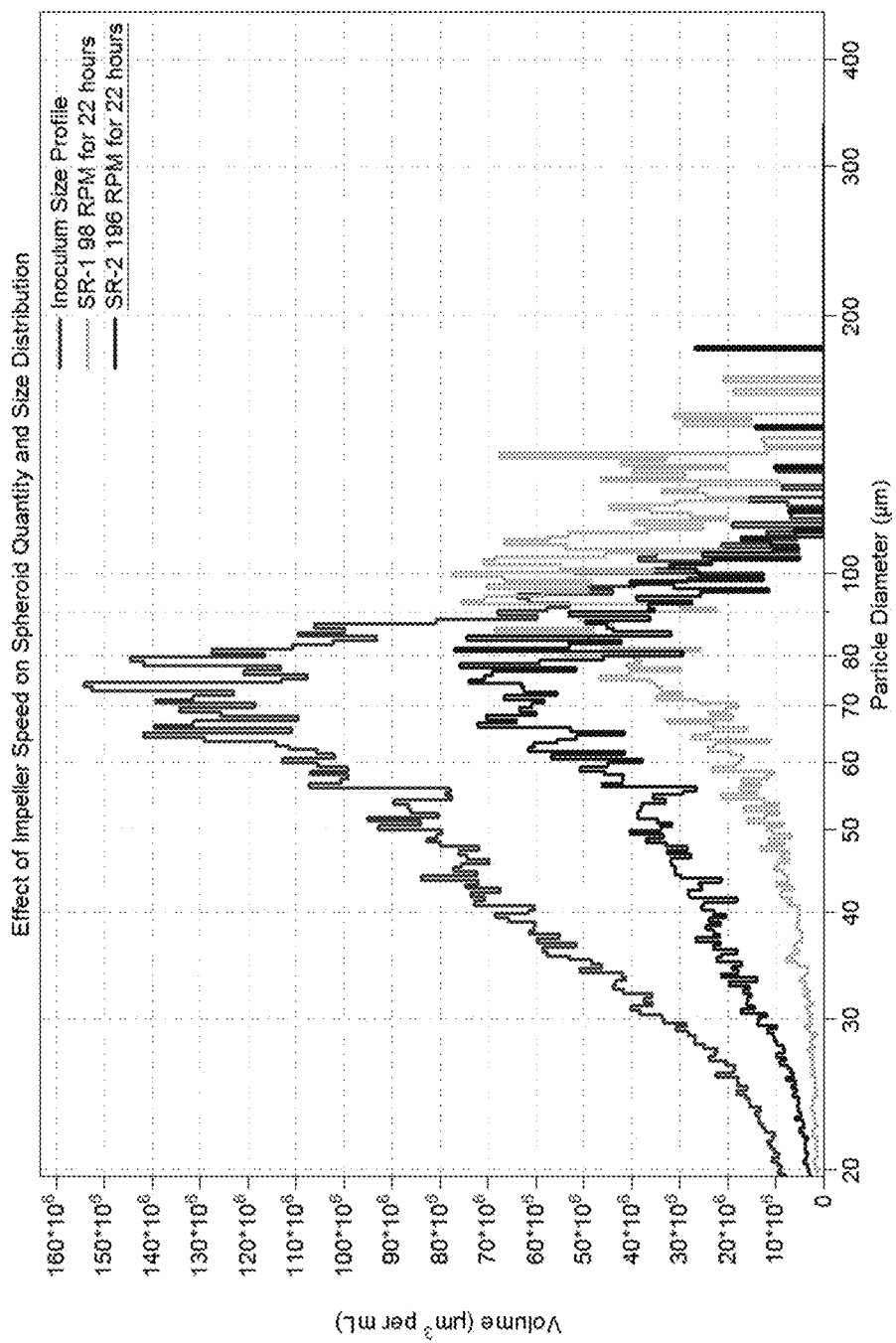
FIGS. 12(a)-12(c): Effect of rotational speed of spinner reservoir. (a) Effect of impeller speed on spheroid quantity and size distribution; (b) micrographs of spheroids after 22 hours of mixing; and (c) caspase activity normalized for spheroid volume. These figures show that a rapid speed of spinning of 196 RPM vs. 98 PRM can have a favorable effect on forming spheroids of smaller size without the adverse effect of cell death since caspase 3/7 activity and Fluoroquench™ vital staining of hepatocytes is comparable at both rates of spinning.
Figure 12B:
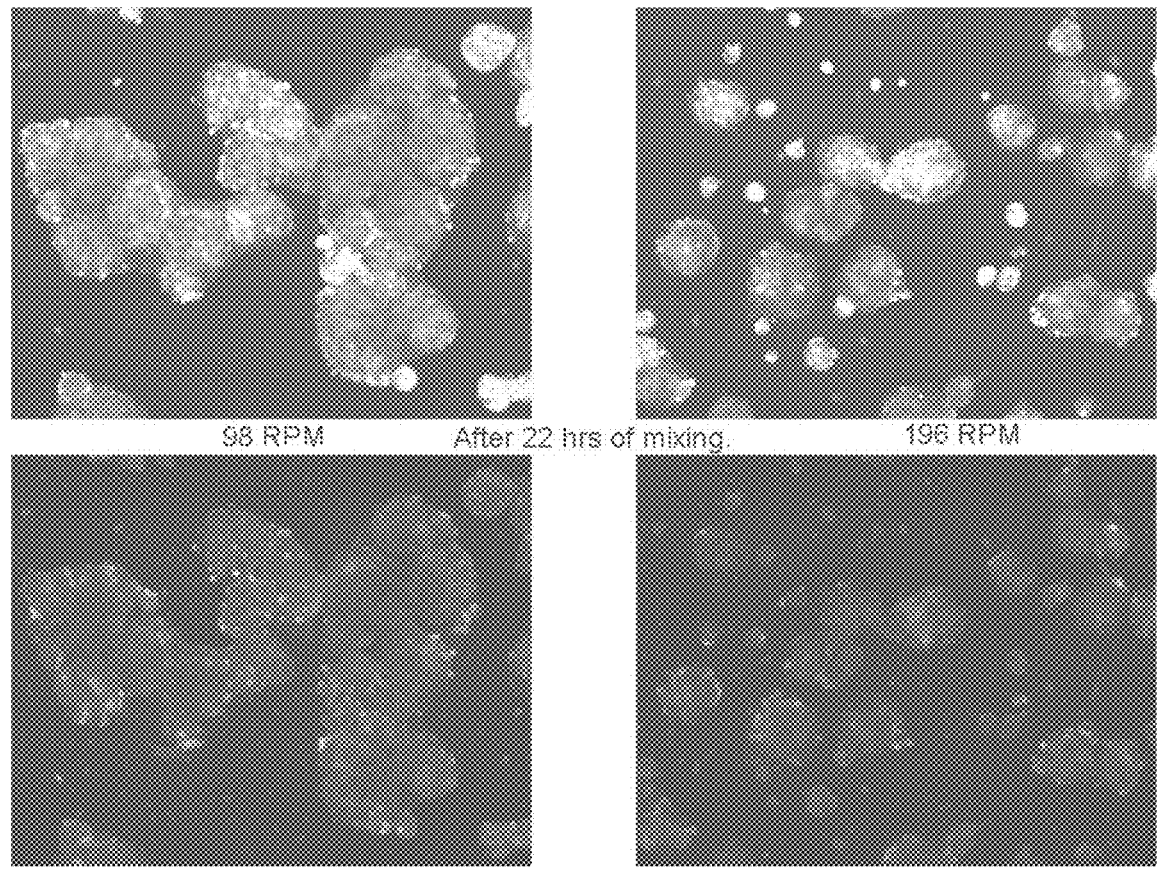
Figure 12C:
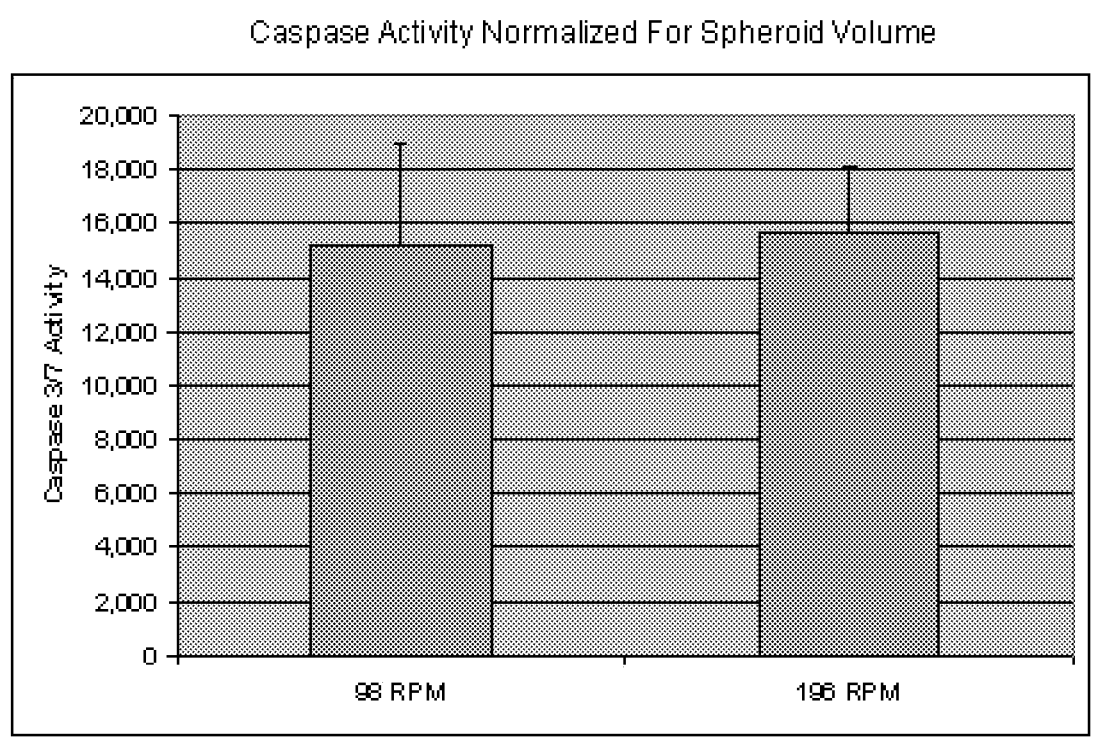

Two 1.5 L rocker boxes were inoculated with 1 liter of hepatocyte suspension ($5 \times 10^6$ cells/mL) and cultured for 24 hours (red line). Spheroids were divided and re-suspended in 2 liters of fresh media and inoculated into one of two SRBAL spin reservoirs. One reservoir was agitated at 98 rpm (green line) and the other at 196 rpm (blue line) for 22 hours. At the end of 22 hours, 20 mL of spheroid suspension was removed from each reservoir, pelleted, suspended in fresh media and inoculated into glass rocker plates. Samples for albumin production and BUN were taken at 4 hours and 24 hours. The results of this study are shown in FIG. 12.

These results demonstrate that faster spinner rates can lead to smaller spheroids, which can be advantageous under some conditions. These results also demonstrate that slower spinner rates can lead to larger spheroids, which can settle faster in a settling column and can be less likely to exit the settling column.

Figure 13:
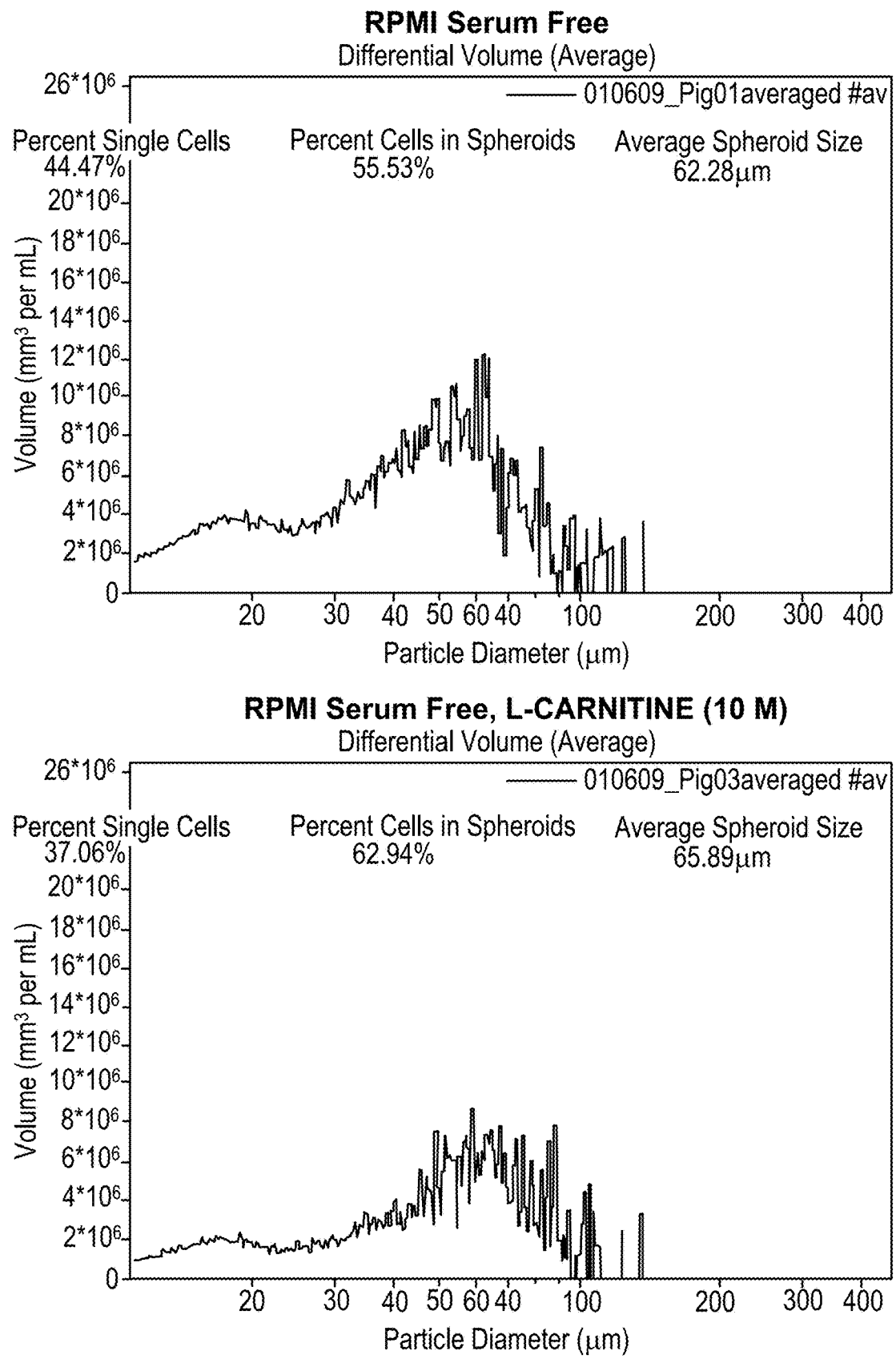
FIG. 13: Formation of spheroids in both serum-containing and serum-free medium. Spheroids form in both serum free medium and medium supplemented with 10% FBS. L-carnatine can have a favorable effect on spheroid formation.
Figure 13:
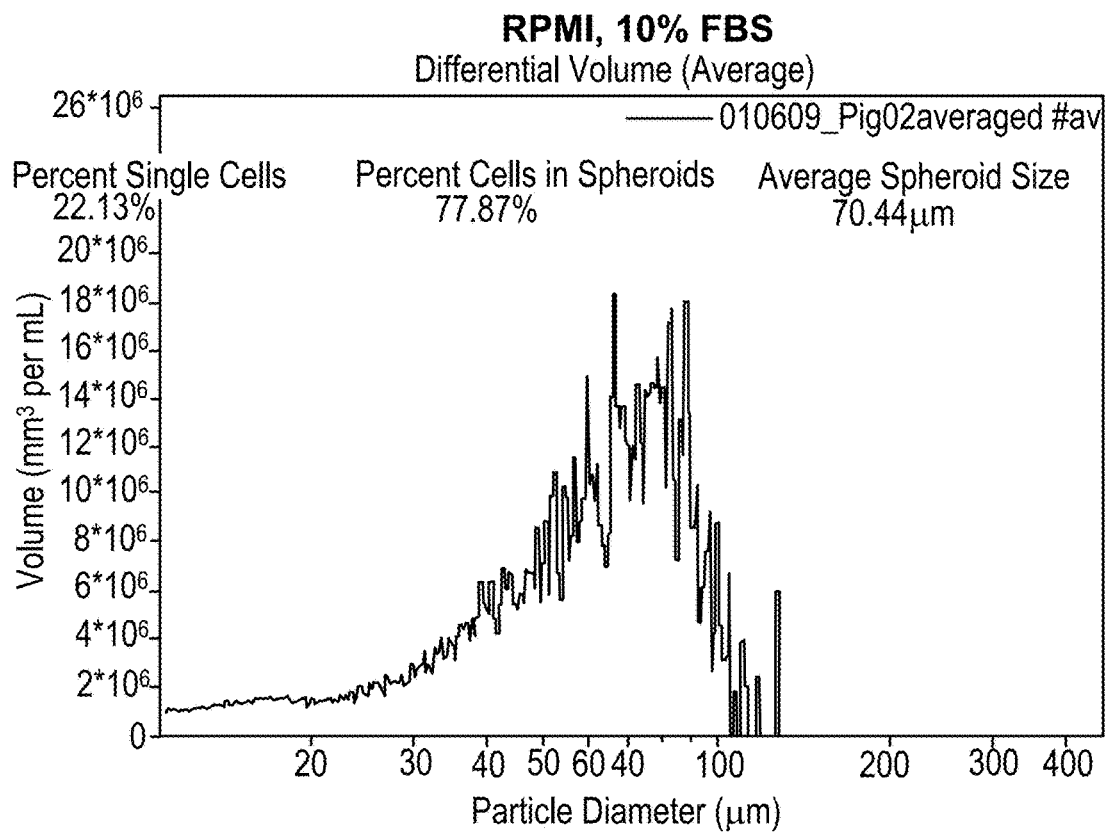
Figure 13:
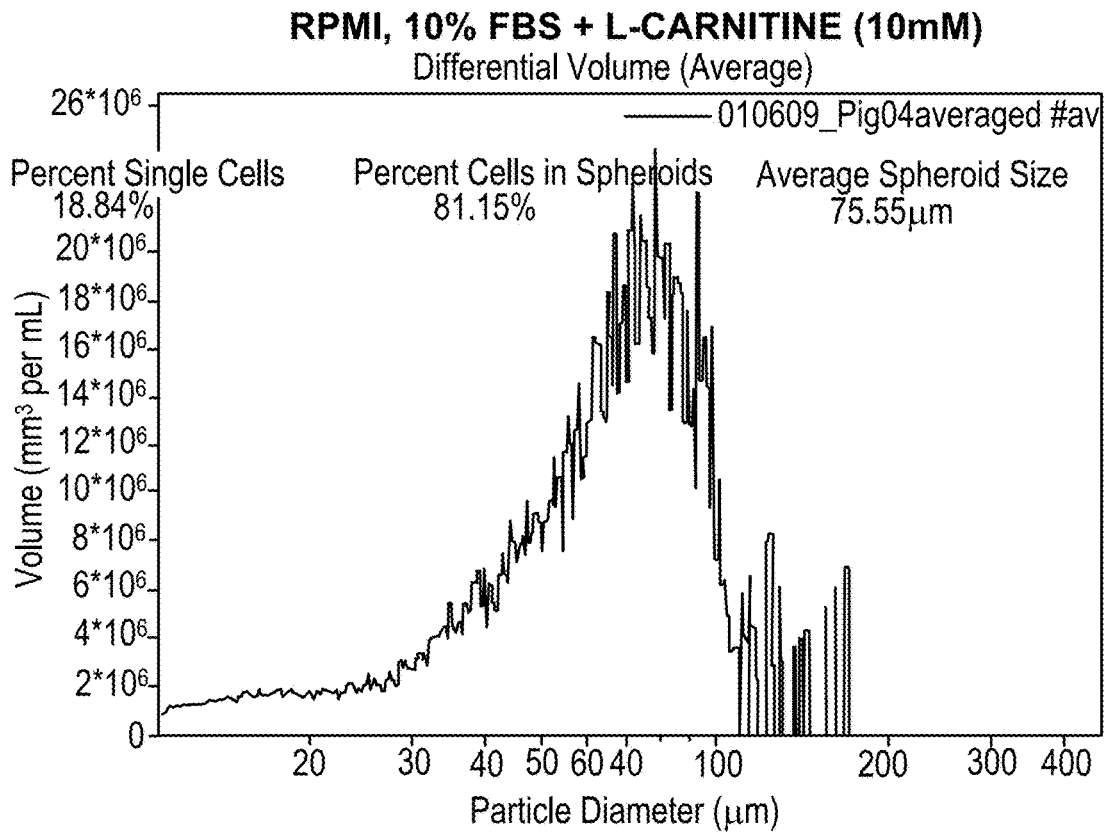

Example 7: Formation of Spheroids in Both Serum-Containing and Serum-Free Medium As shown in FIG. 13, spheroids can be formed both in medium that has serum and in medium that is serum-free. There appears to be a benefit of adding 10% calf serum and 10 mM L-carnitine to medium during spheroid formation. For example, 81% of hepatocytes were incorporated into spheroids when RPMI spheroid forming medium was supplemented with 10% FBS and 10 mM L-carnitine and a suspension of freshly isolated pig hepatocytes was rocked at 0.25 Hz for 24 hours.

Example 8: To Establish Efficacy of the SRBAL in a Preclinical Model of ALF by Demonstrating Improved Survival and a Reversal of Hepatic Encephalopathy 1. A Dose Response Study of the SRBAL Using Xenogeneic (Pig) Hepatocytes The efficacy of the SRBAL in ALF is assessed in two sets of experiments (xenogeneic dose study, allogeneic study). Recipient model, BAL conditions and endpoints for each of these two experiments are summarized in Table 3. The Dose study is intended to determine the optimal number of hepatocytes in the SRBAL and whether there is a synergism between albumin dialysis and hepatocytes in the perfusate circuit. The allogeneic study is to determine if there is additional benefit to using hepatocytes from the same species as the patient. The perfusate circuit in both studies includes physiological levels of albumin (5 g %) along with charcoal and resin columns used commercially in MARS™ albumin dialysis. The SRBAL can be operated at conditions of high flux (50 mL/min) using the 150 kD or 400 kD MWCO modified polysulfone hollow fiber membrane. Dose studies use fresh pig hepatocytes ranging from 0 to 400 grams. The 0 gram group is comparable to standard albumin dialysis. A no BAL control group is included to assess the baseline inflammatory response of ALF dogs in the absence of an extracorporeal device, which may elicit an inflammatory response as suggested in FIG. 5. The allogeneic study uses the same dose of hepatocytes found to be most efficacious in the dose study but allogeneic. Survival duration is the primary endpoint of both the dose study and allogeneic study. Other secondary endpoints listed in Table 3 are carefully monitored and reported.

TABLE 3

Summary of Studies to Test Efficacy of SRBAL

| | Xenogeneic Dose Study (n = 10/group) | Allogeneic Study (n = 5/group) |
|---|---|---|
| Recipient Model | | |
| D-galactosamine-Induced ALF dog | x | x |
| BAL Conditions ** | | |
| Pig Spheroids 400 g + 5 g % Albumin | x | |
| Pig Spheroids 200 g + 5 g % Albumin | x | |
| No Spheroids 0 g + 5% Albumin | x | |
| Dog Spheroids ? g + 5 g % Albumin | | x |
| No BAL | x | |
| Endpoints | | |
| Survival (hours) | x [a] | x [a] |
| Intracranial pressure (mmHg) | x | x [b] |
| Cerebral microdialysis (glycerol, glucose, lactate, ammonia) | x | x [b] |
| Pulmonary Function (arterial pO2, pCO2) | x | x |
| Renal Function (serum Cr, urine output) | x | x |
| SIRS markers (TNFα, IL6) | x | x |
| Liver Injury (ALT, ammonia, glucose, lactate) | x | x |
| Hemodynamics (MAP, HR) & Temperature | x | x |
| Hepatocyte Viability (pre vs. post) | x | x |
| Biochemical Performance of SRBAL [b] | x | x |
| Autopsy (liver, lungs, kidney, brain) | x | x |

[a] primary endpoint
[b] assessed by ureagenesis, albumin production (pre vs. post), O$_2$ consumption (during)
? Optimal dose of allogeneic hepatocyte spheroids will depend on outcome of the Xenogeneic Dose Study Efficacy testing of the SRBAL is conducted in the canine D-galactosamine model of ALF (see, e.g., Sielaff T D, Nyberg S, Amiot B, Hu M, Peshwa M, Wu F, Hu W-S, et al. Application of a bioartificial liver (BAL) in a new model of acute fulminant hepatitis. Surgical Forum 1993; 44:61-63; Nyberg S, Cerra F, Gruetter R. Brain lactate by magnetic resonance spectroscopy during fulminant hepatic failure in the dog. Liver Transplantation and Surgery 1997; 4:158-165). This animal model is selected because of its similarity (hepatic encephalopathy progressing to cerebral edema and brain death, pulmonary edema, hepatorenal syndrome) to clinical ALF. Dogs are instrumented to monitor changes in hemodynamics (pulmonary function, renal function and brain physiology) during development of liver failure (and reversal by SRBAL). Endpoints used for monitoring efficacy of the SRBAL include: 1) survival time, 2) intracranial pressure and cerebral microdialysis as measures of cerebral edema, 3) pulmonary and renal function as other extrahepatic manifestations of ALF, 4) hemodynamics of the animal, 5) levels of TNFα and IL6 as markers of SIRS, and 6) ALT/ammonia/glucose/lactate as markers of liver injury and function. Hepatocyte viability and biochemical performance of porcine hepatocyte spheroids is assessed before, during and after treatment as an indirect measurement of immune protection. Finally, an autopsy is performed on each animal to carefully examine brain, lungs and kidney as well as consistency of liver damage in study animals. A direct correlation may be seen between liver failure, toxin accumulation and extrahepatic manifestations of liver failure, and improvement if this sequence of events is reversed by SRBAL therapy. There may be a synergism between hepatocytes and albumin dialysis.

As in Examples 1 and 2 provided herein, dogs are intubated and instrumented under isoflurane anesthesia before administration of D-galactosamine at T=0 hours. Perfusion of the extracorporeal circuit is initiated at T=12 hours after administration of D-galactosamine. The SRBAL has been under in vitro conditions for at least 24 hours to insure proper formation of spheroids and maximum biochemical performance at the initiation of treatment. Ammonium chloride bolus is administered at 6 hour, 18 hour and continuously after 24 hours to assess ammonia detoxification activity before liver failure, after liver failure, and during SRBAL therapy.

The spheroid reservoir design is suited for these studies since the design allows continuous sampling of hepatocytes for viability and medium for measurement of oxygen consumption before, during, and after treatment. Biochemical performance of SRBAL is measured at baseline (before treatment) and for 24-hours after completion of therapy. Animals are treated up to 48 hours.

A power analysis is performed using data from Table 1 above to establish group size for efficacy testing in this study. According to Table 1, control ALF dogs had a survival of (35, 36, 40, 41 hours, mean—38 hours, st dev—3 hours). Therefore, assuming an alpha of 0.05 and 80% power, the following differences in mean survival between treatment and control groups are significant: 6.3 hours if n=5; 4.5 hours if n=8; and 3.0 hours if n=10. A more conservative mean survival difference of 3 hours and n=10 dogs per group is chosen since Table 1 was limited to only 4 control dogs. These assumptions are valid based on the studies in the Examples.

40 dogs are treated. There is a synergistic effect of albumin dialysis+spheroid hepatocyte therapy at both low (200 gram) and high (400 gram) doses of pig hepatocytes. The longest survivors are in the 400 gram pig spheroid treatment group. Therapy with all three treatments (AD alone, AD+200 gm, AD+400 gm) may be associated with improvement in secondary endpoints such as lower intracranial pressure, normalized cerebral microdialysis values, improved pulmonary and renal function, and reduced systemic inflammation based on lower values of TNFα and IL6.

If the dose of 2.0 gm/kg D-galactosamine is too high and results in lethal ALF beyond the level that can be stabilized by SRBAL therapy, a lower dose of 1.0-1.5 gm/kg D-galactosamine may be used instead. The SRBAL can be operated at conditions of high flux (50 mL/min) using the 150 kD MWCO modified polysulfone hollow fiber membrane. If hepatocyte viability is high at the end of therapy but the benefit of therapy is below expectation (non-significant survival benefit), the system can then be revised to the 400 kD MWCO. If such changes are required, then additional animals are studied such that n=10 per group.

2. The Therapeutic Benefit of Allogeneic Hepatocytes in the SRBAL

The same study as #1 is performed except that dog hepatocytes are used in the SRBAL device. The techniques for isolating hepatocytes from dogs and pigs are identical. The dose of hepatocytes loaded in the SRBAL equals the dose found to be most efficacious in #1. 5 dogs are studied in order to determine if there is an incremental benefit of using hepatocytes from an allogeneic source in the SRBAL.

Results similar to those in #1 may be achieved with allogeneic and xenogeneic hepatocytes at the same dose. Since immune-mediated complications can be less likely with an allogeneic source of hepatocytes, hepatocyte viability may be higher when examining post treatment. The 400 kD hollow fiber membrane is used in the allogeneic study which may improve the efficacy of therapy—longer survival duration.

Example 9: Determine the Role of a Cell-Based Bioartificial Liver in Quenching the Systemic Inflammatory Response Syndrome of Acute Liver Failure (Sirs of Alf)

1. Screen Portal Vein, Hepatic Vein, and Arterial Blood of BAL Treated and Untreated ALF Dogs for Evidence of TLR4 Agonist Activity Dogs from Example 1 provide blood samples that are screened for measurement of TLR4 agonist activity before and every six hours during onset of D-gal-induced ALF. These blood samples are obtained from the portal vein, hepatic vein, and femoral artery of SRBAL treated dogs and untreated control dogs. Two weeks prior to induction of ALF, dogs undergo a surgical procedure to place two BARD™ port-style catheters in the hepatic vein and portal vein. This procedure involves a laparotomy under general anesthesia to place the internal end of the catheter into the appropriate vein. The external portion of the catheter is tunneled to a site on the dog's back for subcutaneous placement of the port. This surgical procedure is more reliable than catheter placement by percutaneous radiological technique. A two week interval between catheter placement and induction of liver failure allows full recovery of the dog without interference from the inflammatory response of laparotomy. Femoral artery catheters are placed by percutaneous technique the day of D-galactosamine infusion. Ports are also accessed by Huber needle at that time.

TLR4 agonist activity are measured by an in vitro assay using HEK293/Luc(+)/TLR4(+) cells (see, e.g., Akira S, Takeda K. Toll-like receptor signaling. Nat Rev Immunol 2004; 4:499-511). This assay, as well as the TLR4 receptor complex, is illustrated in FIGS. 7a-b. Luciferase reporter gene signal are quantified by TD-20/20 luminometer (Turner Designs, Sunnyvale, Calif.). Activation of NFκβ is reported as a ratio of firefly luciferase activity to the constitutively expressed Renilla luciferase internal control from a mean of triplicate wells (see, e.g., Brunn G, Bngm M, Johnson G, Platt J. Conditional signaling by Toll-like receptor. FASEB J 2005; 19:872-4).

The development of acute liver failure may be associated with a SIRS response and a rise in TLR4 agonist activity in systemic arterial blood samples. A rise in TLR4 agonist activity may be seen in blood sampled from portal vein and hepatic vein. There may be differences in profiles of TLR4 agonist activity depending on whether the gut or the liver is the primary source of TLR4 activators. TLR4 activity may show an early rise in portal vein followed by a late sustained rise in hepatic vein blood as liver injury becomes established. SRBAL therapy may be associated with normalization of TLR4 agonist activity since normalization of TNFα—a sensitive marker of systemic activation—may be observed during SRBAL therapy.

2. ECM Components Released During Liver Injury are Mediators of SIRS and these Potential Mediators of SIRS are Cleared During Therapy with the SRBAL Blood samples from portal vein, hepatic vein, and femoral artery obtained from ALF dogs of Example 8 (with or without SRBAL therapy) are screened for presence of TLR4 agonist activity using our HEK293/Luc(+)/TLR4(+) cell in vitro assay. Samples found to have positive TLR4 agonist activity are further analyzed to determine if this activity is related to the presence of LPS, heparan sulfate, and/or hyaluronic acid. These studies are conducted sequentially. The first step is to remove LPS and retest samples with and without LPS removal. The second step is to remove heparan sulfate and retest samples with and without heparan sulfate removal. The third step is to remove hyaluronic acid and retest samples with and without hyaluronic acid removal. A decline in TLR4 agonist activity after any of these three manipulations confirms the presence of that molecule (LPS, heparin sulfate, or hyaluronic acid) in the sample of dog blood, and more importantly, implicates that molecule as a mediator of the SIRS response in ALF. Removal of LPS is performed by incubating the sample in polymixin B, a positively charged detergent which binds LPS specifically (see, e.g., Rifkind D. Studies on the interaction between endotoxin and polymyxin B. J Infectious Dis 1967; 117: 433-438). Removal of heparan sulfate is performed by incubating the sample in recombinant heparanase (see, e.g., Brunn G, Bngm M, Johnson G, Platt J. Conditional signaling by Toll-like receptor. FASEB J 2005; 19:872-4). Removal of hyaluronic acid are performed by incubating the sample in bovine testes hyaluronidase (Sigma Chemicals) (see, e.g., Termeer C C, Hennies J, Voith U, Ahrens T, Weiss J M, Prehm P, Simon J C. Oligosaccharides of hyaluronan are potent activators of dendritic cells. J Immunol 2000; 165: 1863-1870). All materials used in cell culture are certified endotoxin free or tested by the Limulus amebocyte lysate assay gel clot method (Seikagaku, Falmouth Mass.) to assure absence of detectable endotoxin (<0.1 ng/mL).

It may be shown that the SIRS of ALF is mediated, at least in part, by endogenous molecules such as heparan sulfate or hyaluronic acid.

Serum obtained in the course of ALF may contain matrix metalloproteases which cleave extracellular matrix proteins and potentiate TLR4 activation by endogenous or microbial ligands such as LPS. To test whether ALF serum contains these enzymes, HEK/Luc(+)/TLR4(+) cells are cultured on extracellular matrix-coated plates in the presence of ALF serum. Six hours later increasing amounts of LPS are added to separate wells of the cultured cells. Potentiation of TLR4 signaling by ALF serum is detected by a left-ward shift of the LPS-TLR4 activation dose-response curve, and indicates that ALF serum contains an indirect activator or potentiator of TLR4 signaling. If LPS, heparan sulfate, and hyaluronic acid are not found in ALF dog serum, then other potential candidate molecules are considered. Other candidates include lauric acid, fibrinogen, fibronectin, heat shock protein, and (β-defensin. Heparan sulfate and hyaluronic acid are leading candidates.

3. The Influence of Hepatocytes, Kupffer Cells, and Stellate Cells of the Liver on the Circulating Levels of ECM Components in ALF and the Roles of these Cells in Regulating the SIRS of Acute Liver Failure This experiment includes a series of in vitro studies to determine the role of liver cells in regulating the SIRS response of ALF. Plasma samples with TLR4 agonist activity obtained from control ALF dogs (no BAL group) of Example 8 are studied. Portal vein, hepatic vein and femoral artery samples are considered. TLR4 agonist activity are determined in these samples using a HEK293/Luc(+)/TLR4 (+) cell in vitro assay (see, e.g., Brunn G, Bngm M, Johnson G, Platt J. Conditional signaling by Toll-like receptor. FASEB J 2005; 19:872-4). Rat liver cells are used in the studies (see, e.g., Seglen P. Preparation of isolated rat liver cells. Methods in Cell Biology 1976; 13:29-83), and the results are verified using porcine hepatocytes. Crude preps of liver cells (85-90% hepatocytes, 5-10% Kupffer cells, stellate cells, etc.) are used in initial studies, followed by enriched preps of hepatocytes, Kupffer cells or stellate cells in subsequent studies. Primary hepatocytes are enriched by selective culture of crude preps in arginine-free medium available from Sigma Chemical (see, e.g., Leffert H L, Paul D. Studies on primary cultures of differentiated fetal liver cells. J Cell Biol 1972; 52:559-568; Spiegelberg T, Bishop J O. Tissue-specific gene expression in mouse hepatocytes cultured in growth-restricting medium. Mol Cell Biol 1988; 8:3338-3344). Kupffer cells are isolated by a four step technique employing enzymatic treatment, density gradient centrifugation, centrifugal elutriation, and selective adherence (see, e.g., Valatas V, Xidakis C, Roumpai H, Kolios G, Kouroumalis E. Isolation of rat Kupffer cells: a combined methodology for highly purified primary cultures. Cell Biol International 2003; 27:67-73). Stellate cells are isolated by density gradient centrifugation using arabinogalactan (see, e.g., Ramm G. Isolation and culture of rat hepatic stellate cells. J Gastroenterol Hepatol 1998; 13:846-851). Enriched cell populations ($1 \times 10^6$ cells/mL) are incubated at 37° C. for 24 hours in a serum free medium of RPMI, supplemented with insulin/transferring/selenium (ITS, Sigma Chemical) and 0.5 vol % dog serum sample. Dog serum samples (0.5 vol %) are also incubated at 37° C. for 24 hours in a control condition of serum free medium without cells. TLR4 agonist activity are measured in both cell and no-cell (control) conditions to determine the effect of liver cell exposure on TLR4 agonist activity. TNFα levels are measured in all Kupffer cell cultures and any samples that show a paradoxical increase in TLR4 agonist activity.

A decline in TLR4 agonist activity may be seen after incubation of dog sample in crude and pure cultures of primary hepatocytes due to metabolic degradation of mediators of the SIRS response. A reduction in TLR4 agonist activity may also be seen after incubation in cultures of pure Kupffer cells or pure stellate cells.

If the 0.5 vol % concentration of "toxic" sample is large enough to stimulate a TLR4 agonist response in HEK293/Luc(+)/TLR4(+) cell, higher concentrations of toxic dog serum are tested (1-10 vol %). If ALF dog serum contains matrix metaloproteases, techniques of LPS titration are employed to rule out contamination in this experiment if indicated. If small numbers of dendritic cells, known to express TLR4 and which are present in the spheroid aggregates, participate in the quenching of SIRS of ALF, the role of dendritic cells in the SRBAL are considered if the beneficial results of SRBAL therapy cannot fully explained by removal of hepatocytes, Kupffer cells, and stellate cells.

Example 10: Determine the Role of Hepatocyte Nuclear Factor 6 (Hnf6) in Maintaining Ureagenesis in a Spheroid Reservoir Bioartificial Liver 1. A Recombinant Adenoviral Vector to Induce Stable Expression of HNF6 in Rat Hepatocyte Spheroids A CMV-GFP-HNF6 fusion expressing adenovirus plasmid (AdCMV-GFP-HNF6) is designed based on a cDNA clone containing the entire protein coding sequence of rat Hnf6 generated by polymerase chain reaction amplification using rat hepatocyte cDNA. To control adverse effects of adenovirus infections, a GFP containing adenovirus plasmid (AdCMV-GFP), without Hnf6, is also be prepared. Rats are infected with stepwise incremental concentrations of AdCMV-GFP-HNF6 until the optimal concentration of adenovirus is found which successfully expresses HNF6-GFP in the majority of hepatocytes. Once this has been established, hepatocytes are isolated from uninfected, control infected (AdCMV-GFP) and AdCMV-GFP-HNF6 from male Sprague-Dawley rats (Harlan, Indianapolis, Ind.) by a two-step perfusion method (see, e.g., Seglen P. Preparation of isolated rat liver cells. Methods in Cell Biology 1976;

13:29-83). Only harvests yielding hepatocytes with a viability of at least 90%, as determined by trypan-blue dye exclusion, are used for subsequent hepatocyte spheroid cultures. Spheroid hepatocyte cultures are prepared by incubation of freshly isolated cells in siliconized 20 mL glass culture plates at a cell density of 1×10$^6$ cells/mL under rocked conditions (see, e.g., Brophy C, Luebke-Wheeler J, Amiot B, Remmel R, Rinaldo P, Nyberg S. Rat hepatocyte spheroids formed by rocked technique maintain differentiated hepatocyte expression and function. Hepatology, 2009, 49:578-86). Samples are harvested 1, 2, 7 and 14 days for subsequent experiments. Changes in HNF6 expression are monitored by green fluorescence microscopy due to the fusion of green fluorescent protein with HNF6. Flow cytometry is used to determine the percentage of hepatocytes stably expressing GFP-HNF6. Briefly, spheroids from adenovirus treated and untreated cultures are trypsinized and immediately analyzed to determine the ratio of green fluorescent cells compared to total cell number. Changes in Hnf6 expression due to adenoviral HNF6 infections are also verified by reverse transcription polymerase chain reaction (qRT-PCR) (see, e.g., Brophy C, Luebke-Wheeler J, Amiot B, Remmel R, Rinaldo P, Nyberg S. Rat hepatocyte spheroids formed by rocked technique maintain differentiated hepatocyte expression and function. Hepatology, 2009, 49:578-86). In addition, changes in HNF6 protein are monitored by Western blot analyses using an HNF6 antibody from the multiple rat liver infected with either the control or HNF6 expressing adenoviruses compared to uninfected cultures from isolated adult rat livers.

Hnf6 expression may be induced and maintained in rat hepatocyte spheroids since the expression of Hnf6 is under direct control of the CMV promoter. Hnf6 expression may be detected by quantitative qRT-PCR analyses of Ad-CMV-HNF6 expressing hepatocytes and not by Ad-CMV infected hepatocyte spheroids which could lose expression of Hnf6 over 14 days in culture. Increases in HNF6 protein, determined by Western blot analyses, may follow increases in Hnf6 gene expression.

If it is difficult to obtain HNF6 expressing cells by tail vein injection of an HNF6 expressing adenovirus, hepatocytes are directly infected under in vitro suspension culture conditions. Alternatively, HNF6 is re-expressed in rat hepatocyte spheroid cultures directly by transiently transfecting CMV-HNF6 expressing plasmid into suspensions of primary rat hepatocytes.

2. The Effect of Overexpression of HNF6 on Expression of Urea Cycle Genes and their Function in Rocked Spheroid Culture Rat hepatocyte spheroid cultures from uninfected, Ad-CMV infected (as controls) and Ad-CMV-HNF6 infected rat livers are performed as described above in #1. Initially, qRT-PCR analyses of all six ureagenesis genes are done to determine the effects of HNF6 on ureagenesis gene expression. In order to detect biochemical performance of the hepatocyte spheroids, culture media are spiked with ammonia sulfate and detoxification rates are measured. The conversion of heavy ammonia ($N^{15}D_3$) to heavy urea is used to detect complete urea cycle activity.

Cells which express HNF6 may have improved ammonia detoxification abilities compared to untreated or control infected cultures which do not express HNF6. Changes in ureagenesis function may be due to increases in the expression levels of ureagenesis genes.

If forced expression of HNF6 is sufficient to induce changes in ureagenesis gene expression and function, other liver transcription factors are studied to determine if additional regulatory factors are lost in hepatocyte spheroids. This is accomplished by qRT-PCR analyses of the expression of other hepatocyte transcription factors that are involved in the regulation of ureagenesis gene expression.

3. HNF6 can Regulate Cps1 Expression

Both Hnf6 and Cps1 expression is down regulating in hepatocyte spheroid cultures. This study involves a combination of transient transfection and chromatin immunoprecipitation (ChIP) analyses. For transient transfection analyses, a series of promoter constructs containing portions of the Cps1 upstream regulatory sequences driving the expression of a luciferase reporter gene. An HNF6 expression plasmid is constructed which allows for high levels of expression from the cytomegalovirus promoter (CMV) when transfected into tissue culture cells. These expression plasmids are introduced into NIH3T3 cells along with different fragments of the Cps1 promoter driving luciferase. HNF6 is not normally expressed in NIH3T3 cells so these cells are used to determine whether HNF6 transactivates expression via the Cps1 promoter by measuring relative luciferase levels. A comparison of the different promoter fragments to respond to HNF6 transactivation allows for mapping where HNF6 acts on the Cps1 promoter/enhancer. This information may indicate where to focus initial analyses of direct HNF6 regulatory regions. A direct in vivo relationship may be identified between HNF6 and Cps1. To accomplish this adult rat livers and hearts (as a negative control since they do not express HNF6) are isolated and fixed with 1% formaldehyde, cells dissociated using a homogenizer, and chromatin are sheared to approximately 500 bp by sonication. Immunoprecipitation of chromatin is performed using the Upstate ChIP Assay Kit (Upstate #17-295) following the manufacturer's instructions with anti-HNF6 (Santa Cruz, H-100) or anti-Pes1 antibodies. Primers are designed to allow PCR amplification of regions of chromatin that flank a known HNF6 binding site in Cyp7a1, any predicted HNF6 binding sites in Cps1, and a fragment of RNA Pol2, which lacks an HNF6 binding site as a negative control.

HNF6 may be capable of regulating ureagenesis functions by regulating the expression of ureagenesis genes, such as Cps1, in hepatocyte spheroids, and HNF6 can transactivate Cps1 gene expression via upstream Cps1 regulatory regions using transient transfections assays. HNF6 may indirectly regulate the expression of Cps1, and HNF6 may do this through the direct regulation of other transcription factors that directly regulate Cps1 expression. Evidence of in vivo binding of HNF6 may not be found by ChIP analyses. HNF6 may directly exert its regulatory effects on Cps1 expression, and ChIP analyses may allow for identification of potentially novel HNF6 regulatory sequences.

If HNF6 is not sufficient to regulate the expression of Cps1 in NIH3T3 cells, this may be due to the absence of additional liver transcription factors required to transactivate the Cps1 promoter/enhancer in vitro. The transient transfection assay is performed in a hepatoma cell lines such as HepG2 which does express most of the hepatic transcription factors, albeit at lower levels then found in endogenous liver tissue.

Example 11—Spheroid Formation

With regards to conditions for spheroid formation, studies were performed using hepatocytes at three cell densities (2, 5, 10×10$^6$ cells/mL) cultured in medium supplemented with 10% fetal bovine serum. Conditions for spheroid formation that were varied included the rocker rate (8 vs 10 cycles/ min) and oxygen tension within the spheroid forming media (low $pO_2$ 50-60 mm Hg and high $pO_2$ about 300 mm Hg). Based on these conditions, a larger number of spheroids were formed at the slower rocking speed and lower $pO_2$ environment in the rocking container. For example, 95% of the initial inoculant of pig hepatocytes formed spheroids of 40 microns or greater at rocking rate of 8 cycles per minute and low $pO_2$. In contrast, only 86% of pig hepatocytes formed spheroids of 40 micron diameter or greater when rocked at 10 cycles/min in a high $pO_2$ environment. The other two combinations of conditions were associated with 90% spheroid formation. Of note, low $pO_2$ environment should not lead to hypoxic conditions in which oxygen supply does not meet the cellular demand for oxygen. Once the supply/demand condition is met, it appears that increasing oxygen tension has a toxic effect during spheroid formation and later during rocked spheroid culture.

Hepatocytes were isolated from pig liver, and spheroids were formed from these cells by rocker technique at low $pO_2$ 50-60 mm Hg and 8 cycles per minute rocking frequency using the multi-tray rocker shown in FIG. 4b. FIG. 20 demonstrates a high efficiency of spheroid formation with 93.7±2.4% of hepatocytes formed into spheroids after 24 hours and 93.2±1.9% formed into spheroids after 48 hours under these conditions. The total volume of cells in the system also remained relatively constant over this 48 hour interval of spheroid formation as shown in FIG. 19. After 48 hours, formed spheroids were then placed into the fenestrated funnel SRBAL bioreactor shown schematically in FIG. 15a and photographically in FIG. 15b. These spheroids were perfused continuously with culture medium for 24 hours. FIG. 18 summarizes the significant rate of oxygen consumption by hepatocytes during this 72 hour time frame. Of note, oxygen consumption was determined by syringe technique during the first 48 hours, and a direct measure of the difference between inflow and outflow oxygen tension was used to determine oxygen consumption while in the SRBAL during the final 72 hours. The difference in techniques explains the difference in values of oxygen consumption determined on Day 2 (92.6 $\mu molO_2$/min) and SRBAL t=0 hr (42.3 $\mu molO_2$/min) in FIG. 18. Both measurements were taken from the same population of spheroids less than 2 hours apart.

Figure 21:
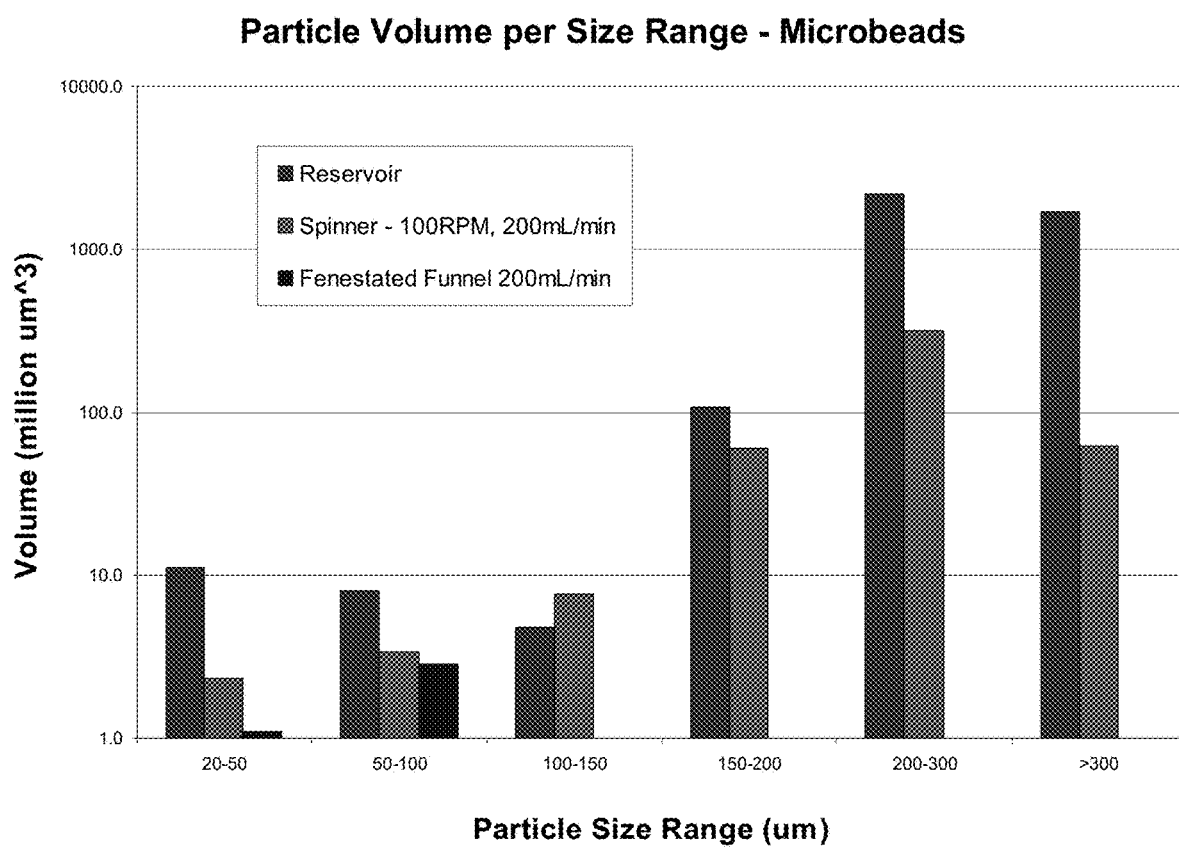
FIG. 21: Graph plotting size distribution of microbead particles in reservoir and outflow line under spinner flask and fenestrated funnel configurations of the SRBAL bioreactor. Large particles were more effectively retained by the fenestrated funnel configuration.

The physical properties of SRBAL designs were tested using a mixture of synthetic microbeads that approximate the same size and density distribution of hepatocyte spheroid preparations. In these studies, microbeads were added to the reservoir. The composition of microbeads in the reservoir and in the outflow line were determined from samples of each using a Coulter counter. The fenestrated funnel design exhibited more effective retention of microbeads in the reservoir with the fewest number of particles exiting in the outflow line. In the experiment shown in FIG. 21, no particles of >100 µm in diameter were observed to exit the reservoir.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A bioartificial liver device comprising a blood separation cartridge in fluid communication with a reservoir chamber, wherein said reservoir chamber comprises hepatocyte spheroids, a means for mixing, a mixing chamber, and a settling volume chamber, wherein said mixing chamber is located below said settling volume chamber and separated from said settling volume chamber by a funnel, wherein said mixing chamber is in fluid communication with said settling volume chamber via an open spout defined in said funnel, wherein said means for mixing is arranged in the mixing chamber and below said open spout, wherein said open spout is located from a bottom, inner surface of said mixing chamber at a distance configured to minimize net loss of said hepatocytes spheroids out of said mixing chamber to said settling volume chamber.

2. The bioartificial liver device of claim 1, wherein said open spout is located less than 5 cm from said bottom, inner surface of said mixing chamber.

3. The bioartificial liver device of claim 1, wherein said funnel comprises openings between 100 µm and 5 mm in diameter.

4. The bioartificial liver device of claim 1, wherein said means for mixing is a magnetic stir bar within said mixing chamber.

5. The bioartificial liver device of claim 1, wherein said mixing chamber comprises an inlet port.

6. The bioartificial liver device of claim 1, wherein said settling volume chamber comprises an outlet port.

7. The bioartificial liver device of claim 1, wherein said funnel comprises more than 25 openings.

8. The bioartificial liver device of claim 7, wherein said openings are between 100 µm and 5 mm in diameter.

9. The bioartificial liver device of claim 1, wherein said reservoir chamber comprises a sampling port.

10. The bioartificial liver device of claim 1, wherein said reservoir chamber comprises temperature probe.

* * * * *